US010227395B2

(12) United States Patent
Chen et al.

(10) Patent No.: US 10,227,395 B2
(45) Date of Patent: Mar. 12, 2019

(54) MONOCLONAL ANTIBODIES THAT NEUTRALIZE ANTHRAX PROTECTIVE ANTIGEN (PA) TOXIN

(71) Applicant: The United States of America, as represented by the Secretary, Department of Health and Human Services, Washington, DC (US)

(72) Inventors: Zhaochun Chen, Potomac, MD (US); Stephen H. Leppla, Bethesda, MD (US); Mahtab Moayeri, Bethesda, MD (US); Suzanne U. Emerson, Gaithersburg, MD (US); Robert H. Purcell, Gaithersburg, MD (US)

(73) Assignee: The United States of America, as represented by the Secretary, Dept. of Health and Human Services, Washington, DC (US)

( * ) Notice: Subject to any disclaimer, the term of this patent is extended or adjusted under 35 U.S.C. 154(b) by 211 days.

(21) Appl. No.: 14/181,099

(22) Filed: Feb. 14, 2014

(65) Prior Publication Data

US 2014/0227257 A1    Aug. 14, 2014

Related U.S. Application Data

(62) Division of application No. 11/793,735, filed as application No. PCT/US2005/046790 on Dec. 21, 2005, now Pat. No. 8,685,396.

(60) Provisional application No. 60/639,074, filed on Dec. 22, 2004.

(51) Int. Cl.
*C07K 16/12* (2006.01)
*A61K 39/00* (2006.01)

(52) U.S. Cl.
CPC .... *C07K 16/1278* (2013.01); *A61K 2039/505* (2013.01); *C07K 2317/21* (2013.01); *C07K 2317/24* (2013.01); *C07K 2317/52* (2013.01); *C07K 2317/622* (2013.01); *C07K 2317/76* (2013.01); *C07K 2319/00* (2013.01)

(58) Field of Classification Search
None
See application file for complete search history.

(56) References Cited

FOREIGN PATENT DOCUMENTS

WO    WO 03/040384 A    5/2003

OTHER PUBLICATIONS

Giusti et al. (Proc. Natl. Acad. Sci. USA. May 1987; 84 (9): 2926-2930).*
Winkler et al (J. Imm., 265:4505-4514, 2000).*
Chien et al. (Proc. Natl. Acad. Sci. USA. Jul. 1989; 86 (14): 5532-5536).*
Caldas et al. (Mol. Immunol. May 2003; 39 (15): 941-952).*
Casadevall et al. (PNAS vol. 109 No. 31, pp. 12272-12273).*
Adams, G.P. et al. (1998) "Increased affinity leads to improved selective tumor delivery of single-chain Fv antibodies." *Cancer Res.* 58:485-490.
Bachmann, M.F. et al. (1997) "The role of antibody concentration and avidity in antiviral protection." *Science* 276:2024-2027.
Brossier, F. et al. (2004) "Functional analysis of Bacillus anthracis protective antigen by using neutralizing monoclonal antibodies." *Infect. Immun.* 72:6313-6317.
Chen, Z. et al., "Efficient neutralization of anthrax toxin by chimpanzee monoclonal antibodies against protective antigen," *J Infect Dis.*, Mar. 2006, 193(5):625-633.
Cirino, N.M. et al. (1999) "Disruption of anthrax toxin binding with the use of human antibodies and competitive inhibitors." *Infect. Immun.* 67:2957-2963.
Collier, R.J. et al. (2003) "Anthrax toxin." *Annu. Rev. Cell Dev. Biol.* 19:45-70.
Cook, G.P. et al. (1995) "The human immunoglobulin $V_H$ repertoire." *Immunol. Today* 16:237-242.
Ehrlich, P.H. et al. (1990) "Potential of primate monoclonal antibodies to substitute for human antibodies: nucleotide sequence of chimpanzee Fab fragments." *Hum. Antibodies Hybridomas* 1:23-26.
Ehrlich, P.H. et al. (1988) "Human and primate monoclonal antibodies for in vivo therapy." *Clin. Chem.* 34: 1681-1688.
Glamann, J. et al. (1998) "Simian immunodeficiency virus (SIV) envelope-specific Fabs with high-level homologous neutralizing activity: recovery from a long-term-nonprogressor SIV-infected macaque." *J. Virol.* 72:585-592.
Greenspan et al., (1999) "Defining epitopes: It's not as easy as it seems," Nature Biotechnology 7:936-937.
Harrison, J.L. et al. (1996) "Screening of phage antibody libraries." *Methods Enzymol.* 267:83-109.
Hull AK et al.: "Human-derived, plant-produced monoclonal antibody for the treatment of anthrax," Vaccine, vol. 23, No. 17-18, Mar. 18, 2005, pp. 2082-2086.
Jackson, H. et al. (1998) "Antigen specificity and tumour targeting efficiency of a human carcinoembryonic antigen-specific scFv and affinity-matured derivatives." *Br. J. Cancer* 78:181-188.
Jernigan, J.A. et al. (2001) "Bioterrorism-related inhalational anthrax: the first 10 cases reported in the United States." *Emerg. Infect. Dis.* 7:933-944.

(Continued)

*Primary Examiner* — Robert A Zeman
(74) *Attorney, Agent, or Firm* — Sheridan Ross PC

(57) ABSTRACT

The present invention relates to monoclonal antibodies that bind or neutralize anthrax protective antigen (PA) toxin. The invention provides such antibodies, fragments of such antibodies retaining anthrax PA toxin-binding ability, fully human or humanized antibodies retaining anthrax PA toxin-binding ability, and pharmaceutical compositions including such antibodies. The invention further provides for isolated nucleic acids encoding the antibodies of the invention and host cells transformed therewith. Additionally, the invention provides for prophylactic, therapeutic, and diagnostic methods employing the antibodies and nucleic acids of the invention.

9 Claims, 8 Drawing Sheets
Specification includes a Sequence Listing.

(56) References Cited

OTHER PUBLICATIONS

Kobiler, D. et al. (2002) "Efficiency of protection of guinea pigs against infection with Bacillus anthracis spores by passive immunization." *Infect. Immun.* 70:544-550.

Krebber, A. et al. (1997) "Reliable cloning of functional antibody variable domains from hybridomas and spleen cell repertoires employing a reengineered phage display system." *J. Immunol. Methods* 201:35-55.

Laffly E. et al.: "Selection of a macaque Fab with framework regions like those in humans, high affinity, and ability to neutralize the protective antigen (PA) of Bacillus anthracis by binding to the segment of PA between residues 686 and 694" *Antimicrobial Agents and Chemotherapy* vol. 49, No. 8, Aug. 2005 (Aug. 2005), pp. 3414-3420.

Lamarre, A. et al. (1991) "Antiidiotypic vaccination against murine coronavirus infection." *J. Immunol.* 147:4256-4262.

Lamarre, A. et al. (1995) "Protection from lethal coronavirus infection by immunoglobulin fragments." *J. Immunol.* 154:3975-3984.

Little, S. F. et al., "Production and characterization of monoclonal antibodies to the protective antigen component of Bacillus anthracis toxin," *Infect Immun*, Jul. 1988, 56(7):1807-13.

Little, S.F. et al. (1996) "Characterization of lethal factor binding and cell receptor binding domains of protective antigen of Bacillus anthracis using monoclonal antibodies." *Microbiology* 142:707-715.

Little, S.F. et al. (1997) "Passive protection by polyclonal antibodies against Bacillus anthracis infection in guinea pigs." *Infect. Immun.* 65:5171-5175.

Liu, S. et al. (2003) "Cell surface tumor endothelium marker 8 cytoplasmic tail-. independent anthrax toxin binding, proteolytic processing, oligomer formation, and internalization." *J. Biol. Chem.* 278:5227-5234.

Maynard, J. A. et al., "Protection against anthrax toxin by recombinant antibody fragments correlates with antigen affinity," *Nat Biotechnol*, Jun. 2002, 20(6):597-601.

Mohamed, N. et al. (2005) "A high-affinity monoclonal antibody to anthrax protective antigen passively protects rabbits before and after aerosolized *Bacillus anthracis* spore challenge." *Infect. Immun.* 73:795-802.

Petosa, C. et al. (1997) "Crystal structure of the anthrax toxin protective antigen." *Nature* 85:833-838.

Pitt, M.L. et al. (2001) "In vitro correlate of immunity in a rabbit model of inhalational anthrax." *Vaccine* 19:4768-4773.

Rosovitz, MJ. et al. (2003) "Alanine-scanning mutations in domain 4 of anthrax toxin protective antigen reveal residues important for binding to the cellular receptor and to a neutralizing monoclonal antibody." *J. Biol. Chem.* 278:30936-30944.

Sawada-Hirai, R. et al., "Human anti-anthrax protective antigen neutralizing monoclonal antibodies derived from donors vaccinated with anthrax vaccine adsorbed," *J Immune Based Ther Vaccines*, May 2004, 2(1):5 (15 pp).

Sblattero, D. et al. (1998) "A definitive set of oligonucleotide primers for amplifying human V regions." *Immunotechnology* 3:271-278.

Schofield, D.J. et al. (2000) "Identification by phage display and characterization of two neutralizing chimpanzee monoclonal antibodies to the hepatitis E virus capsid protein. " *J. Virol.* 74:5548-5555.

Schofield, D.J. et al. (2002) "Four chimpanzee monoclonal antibodies isolated by phage display neutralize hepatitis a virus." *Virology* 292:127-136.

Schofield, D.J. et al. (2003) "Monoclonal antibodies that neutralize HEV recognize an antigenic site at the carboxyterminus of an ORF2 protein vaccine." *Vaccine* 22:257-267.

Schuck, P. (1997) "Use of surface plasmon resonance to probe the equilibrium and dynamic aspects of interactions between biological macromolecules." *Annu. Rev. Biophys. Biomol. Struct.* 26:541-566.

Singh, Y. et al. (1989) "A deleted variant of Bacillus anthracis protective antigen is nontoxic and blocks anthrax toxin action in vivo." *J. Biol. Chem.* 264:19103-19107.

Singh, Y. et al. (1991) "The carboxyl-terminal end of protective antigen is required for receptor binding and anthrax toxin activity." *J. Biol. Chem.* 266:15493-15497.

Skolnick et al., (2000) "From genes to protein structure and function: novel applications of computational approaches in the genomic era," *Trends in Biotechnology* 18:34-39.

Svitel, J. et al. (2003) "Combined affinity and rate constant distributions of ligand populations from experimental surface binding and kinetics and equilibria." *Biophys. J.* 84:4062-4077.

Trill, J.J. et al. (1995) "Production of monoclonal antibodies in COS and CHO cells." *Curr. Opin. Biotechnol.* 6:553-560.

Varughese, M. et al., "Internalization of a *Bacillus anthracis* protective antigen-c-Myc fusion protein mediated by cell surface anti-c-Myc antibodies," *Mol Med*, Feb. 1998, 4(2):87-95.

Varughese, M. et al. (1999) "Identification of a receptor-binding region within domain of the protective antigen component of anthrax toxin." *Infect. Immun.* 67: 1860-1865.

Welkos, S.L. et al. (1988) "Sequence and analysis of the DNA encoding protective antigen of *Bacillus anthracis.* " *Gene* 69:287-300.

Wild, M. A. et al., "Human antibodies from immunized donors are protective against anthrax toxin in vivo," *Nat Biotechnol*, Nov. 2003, 21(11):1305-6.

International Search Report and Written Opinion, dated Aug. 13, 2007, from PCT/US05/46790, filed Dec. 21, 2005.

\* cited by examiner

FIG. 1

| FIG. 1A |
|---------|
| FIG. 1B |

| VH | FR1 | CDR1 | FR2 | CDR2 |
|---|---|---|---|---|
| W1 | EVQLLETGGGLVQPGGSLRLSCAASGFTLR | S**YHMS | WVRRAPGKGLEWVS | VIYD*GGSTSYADSVKG |
| W2 | ----------V------------------- | -**---- | -------K------ | ----*------------ |
| W5 | Q---Q-S-P---K-SQT-S-T--V-ADSIT | SGY-YWN | -I-QP-------IA | Y-DY*RGT-T-NP-L-S |
| A63-6 | ----V-----F-K------V--------FS | D**-A-H | ----Q--E----- | T-SGS-T-W-------- |
| F3-6 | ------V-------R-------------FS | -**-G-H | -----Q-------A | F-AFDE-NQH-----R- |
| F5-1 | ------V-S-AEVKK--E---KI---K----YSFT | N**-WIG | ----QM------MG | S--PGDSD-R-SP-FQ- |

| | FR3 | CDR3 | FR4 |
|---|---|---|---|
| W1 | RFTISRDNSKNTLYLQMTSLRAEDTAVYYCAR | S***GRPLQNYYYMDV | WGKGTTVTVSS |
| W2 | ------------------------------- | -***------------ | ----------- |
| W5 | -V-M-L-T---QFS-KLS-VT-A-------- | GG*****-Y-QYGD*YAWF-P | ---Q------- |
| A63-6 | -------------------N----------- | NPMV-V-QFY---I-- | ----------- |
| F3-6 | ----------------NR--T-------V-- | GRAA-H-GAS*--F-Y | ---Q-P----- |
| F5-1 | QV---A-K-I--A---WS--K-S--I----- | VGIYCS-NTCLAPSG---V | ---N------- |

FIG. 1A

| Vκ | FR1 | CDR1 | FR2 |
|---|---|---|---|
| W1 | EIVMTQSPLSLPVTPGEPASISC | RSSQSLLHSNRYNYLD | WYLQKPGQSPQLLIY |
| W2 | ---------------------- | ---------T----- | --------------- |
| W5 | ---D-------S-----Q----- | K---------DGNT--Y | --------------- |
| A63-6 | ---D-L-----S--SASV-DRVT-T- | -A---GISN*****--A | ---Q----KA-K--- |
| F3-6 | ---D-RL----S--SASV-DRVT-T- | -A---GIST*****W-A | ---Q----RA-KP--- |
| F5-1 | ---D-VL----S--SASL-DRVT-T- | WA---GITT*****R-N | ---QH----KP-K--- |

| | CDR2 | FR3 | CDR3 | FR4 |
|---|---|---|---|---|
| W1 | LGSNRAS | GVPDRFSGSGSGTDFTLKISRVEAEDVGVYC | MQALQTPFT | FGPGTKVEIKR |
| W2 | ------- | ---G-------------------------- | -----L--- | --Q----K---A |
| W5 | RV----- | ---S------------------Q------- | --GI-L-L- | --G--------A |
| A63-6 | YA-KLE- | ---S---------P-Y--T--SLQP--SAT-F- | Q-YSTN-LS | --G---L---A |
| F3-6 | AA--LQ- | ---S---------E----T--SLQP--FAT-- | Q-YNSY-I- | --Q--RL---- |
| F5-1 | DA-RLG- | ---SH--------------T-NSLQP--FAT-F- | Q-FKMY-P- | --Q----D---A |

MONOCLONAL ANTIBODIES THAT NEUTRALIZE ANTHRAX PROTECTIVE ANTIGEN (PA) TOXIN

CROSS REFERENCE TO RELATED APPLICATIONS

This application is a divisional of U.S. patent application Ser. No. 11/793,735, filed on Dec. 8, 2009, issued as U.S. Pat. No. 8,685,396 on Apr. 1, 2014; which is a national stage application under 35 U.S.C. 371 and claims the benefit of PCT Application No. PCT/US05/46790 having an international filing date of 21 Dec. 2005, which designated the United States, which PCT application claimed the benefit of U.S. Provisional Application No. 60/639,074 filed 22 Dec. 2004; for which each of the disclosures are incorporated herein by reference.

FIELD OF THE INVENTION

This invention relates generally to the field of immunology and specifically to monoclonal antibodies that bind or neutralize anthrax protective antigen (PA) toxin.

BACKGROUND OF THE INVENTION

Anthrax has re-emerged as a serious bioterrorist threat. Inhalational anthrax is usually fatal if not identified early enough for antibiotics to be of use. The lethality is primarily due to the effects of the toxins.

Anthrax toxin, which consists of three polypeptides protective antigen (PA or PAw, 83 kDa), lethal factor (LF, 90 kDa) and edema factor (EF, 89 kDa), is a major virulence factor of *Bacillus anthracis*. The LF and EF components are enzymes that are carried into the cell by PA. The combination of PA and LF forms lethal toxin. Anthrax toxin enters cells via a receptor-mediated endocytosis. PA binds to the receptor and is processed (PA, 63 kDa), which forms a heptameric ring that delivers the EF or LF to the cytosol. The path leading from PA binding to cells via TEM-8 or CMG2, furin processing, heptamer formation, LF or EF binding to heptamer, or the translocation of EF/LF to the cytosol provides multiple sites for molecular intervention.

Mouse monoclonal antibodies neutralize anthrax toxin in vivo in rat (Little et al., 1990 *Infect Immun* 58:1606-1613). Rabbit anti-PA given 24 hours post-infection protects 90% of the infected guinea pigs (Kobiler et al. 2002 *Infect Immun* 70:544-550). Domain 4 of PA contains the dominant protective epitopes of PA (Flick-Smith et al. 2002 *Infect Immun* 70:1653-1656). Protection against anthrax toxin by anti-PA monoclonal antibodies correlates strongly with affinity (Maynard et al. 2002 *Nat Biotechnol* 20:597-601).

SUMMARY OF THE INVENTION

The present invention relates to monoclonal antibodies that bind or neutralize anthrax protective antigen (PA) toxin. The invention provides such antibodies, fragments of such antibodies retaining anthrax PA toxin-binding ability, fully human or humanized antibodies retaining anthrax PA toxin-binding ability, and pharmaceutical compositions including such antibodies. The invention further provides for isolated nucleic acids encoding the antibodies of the invention and host cells transformed therewith. Additionally, the invention provides for prophylactic, therapeutic, and diagnostic methods employing the antibodies and nucleic acids of the invention.

BRIEF DESCRIPTION OF THE DRAWINGS

FIG. 1A-B. Alignments of the deduced amino acid sequences of the variable domains of the heavy chains (FIG. 1A) and kappa chains (FIG. 1B) are shown for clones W1, W2, W5, A63-6, F3-6 and F5-1. Substitutions relative to W1 are shown in single amino acid letters. Identical residues are indicated by dashes. Absence of corresponding residues relative to the longest sequence is indicated by stars. Complementarity-determining regions (CDR1, CDR2, and CDR3) and framework regions (FR1, FR2, FR3, and FR4) are indicated above the sequence alignments. VH W1-SEQ ID NO: 1; VH W2—SEQ ID NO: 17; VH W5—SEQ ID NO: 33; VH A63-6—SEQ ID NO: 34; VH F3-6—SEQ ID NO: 35; VH F5-1—SEQ ID NO: 36; Vκ W1—SEQ ID NO: 9; Vκ W2—SEQ ID NO: 25; Vκ W5—SEQ ID NO: 37; Vκ A63-6—SEQ ID NO: 38; Vκ F3-6—SEQ ID NO: 39; Vκ F5-1—SEQ ID NO: 40.

BRIEF DESCRIPTION OF THE SEQ ID NOS

Figure 2A:
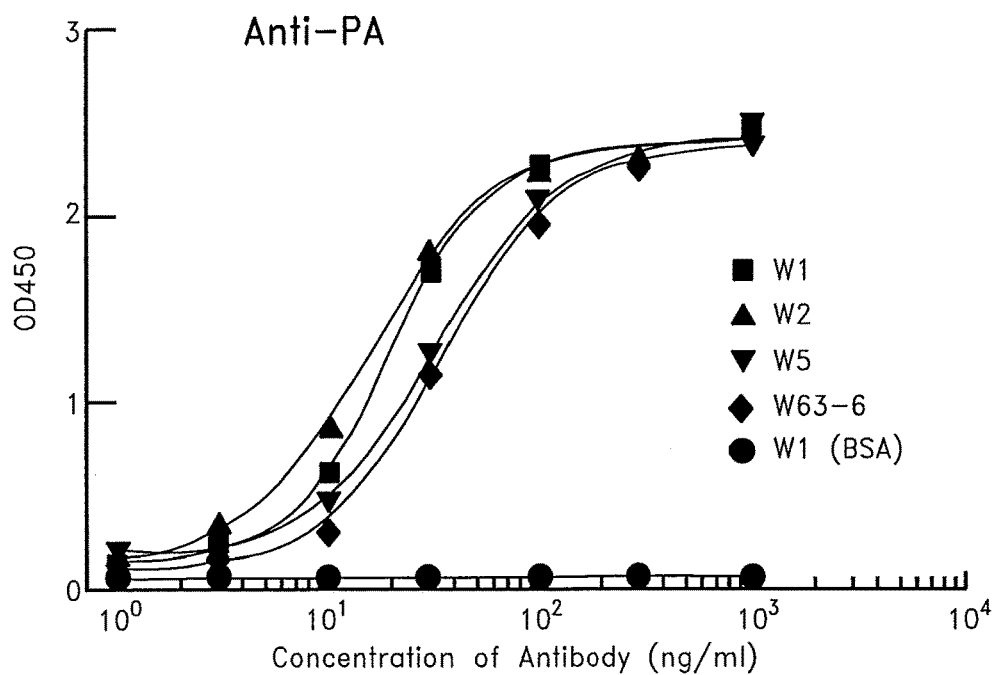
FIG. 2A-B. ELISA titration of anti-PA (FIG. 2A) and anti-LF (FIG. 2B) single-chain Fvs (scFvs). Recombinant PA (FIG. 2A), LF (FIG. 2B), or unrelated proteins, BSA, thyroglobulin, lysozyme, and phosphorylase-b were used to coat the wells of an ELISA plate. Wells were then incubated with various dilutions of scFvs. Bound scFv was detected by the addition of peroxidase-conjugated anti-His antibody followed by TMB substrate. The anti-PA and anti-LF scFvs did not bind to the unrelated proteins as shown in FIG. 2A and FIG. 2B, respectively; only BSA is shown as an example.

| Region | Heavy Chain<br>Anti-PA W1 Sequence<br>SEQ ID NO: 1 | Light Chain<br>Anti-PA W1 Sequence<br>SEQ ID NO: 9 |
|---|---|---|
| FR1 | SEQ ID NO: 2 | SEQ ID NO: 10 |
| CDR1 | SEQ ID NO: 3 | SEQ ID NO: 11 |
| FR2 | SEQ ID NO: 4 | SEQ ID NO: 12 |
| CDR2 | SEQ ID NO: 5 | SEQ ID NO: 13 |
| FR3 | SEQ ID NO: 6 | SEQ ID NO: 14 |
| CDR3 | SEQ ID NO: 7 | SEQ ID NO: 15 |
| FR4 | SEQ ID NO: 8 | SEQ ID NO: 16 |

| Region | Heavy Chain<br>Anti-PA W2 Sequence<br>SEQ ID NO: 17 | Light Chain<br>Anti-PA W2 Sequence<br>SEQ ID NO: 25 |
|---|---|---|
| FR1 | SEQ ID NO: 18 | SEQ ID NO: 26 |
| CDR1 | SEQ ID NO: 19 | SEQ ID NO: 27 |
| FR2 | SEQ ID NO: 20 | SEQ ID NO: 28 |
| CDR2 | SEQ ID NO: 21 | SEQ ID NO: 29 |
| FR3 | SEQ ID NO: 22 | SEQ ID NO: 30 |
| CDR3 | SEQ ID NO: 23 | SEQ ID NO: 31 |
| FR4 | SEQ ID NO: 24 | SEQ ID NO: 32 |

Deposit of Biological Material

The following biological material has been deposited in accordance with the terms of the Budapest Treaty with the American Type Culture Collection (ATCC), Manassas, Va., on the date indicated:

| Biological material | Designation No. | Date |
|---|---|---|
| Chimpanzee Anti-Anthrax PAW1 Fab Fragment in pcomb3H Vector | PTA-6293 | Nov. 10, 2004 |

Chimpanzee Anti-Anthrax PAWL Fab Fragment in pcomb3H Vector was deposited as ATCC Accession No. PTA-6293 on Nov. 10, 2004 with the American Type Culture Collection (ATCC), 10801 University Blvd., Manassas, Va. 20110-2209, USA. This deposit was made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposit. The deposit will be made available by ATCC under the terms of the Budapest Treaty, and subject to an agreement between Applicant and ATCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14). Availability of the deposited biological material is not to be construed as a license to practice the invention in contravention of the rights granted under the authority of any government in accordance with its patent laws.

| Biological material | Designation No. | Date |
|---|---|---|
| Chimpanzee Anti-Anthrax PAW2 Fab Fragment in pcomb3H Vector | PTA-6049 | Jun. 4, 2004 |

Chimpanzee Anti-Anthrax PAW2 Fab Fragment in pcomb3H Vector was deposited as ATCC Accession No. PTA-6049 on Jun. 4, 2004 with the American Type Culture Collection (ATCC), 10801 University Blvd., Manassas, Va. 20110-2209, USA. This deposit was made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposit. The deposit will be made available by ATCC under the terms of the Budapest Treaty, and subject to an agreement between Applicant and ATCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14). Availability of the deposited biological material is not to be construed as a license to practice the invention in contravention of the rights granted under the authority of any government in accordance with its patent laws.

DETAILED DESCRIPTION OF THE PREFERRED EMBODIMENT

Passive immunization using monoclonal antibodies from humans or non-human primates represents an attractive alternative for prevention of anthrax. Monoclonal antibodies to anthrax protective antigen (PA) were recovered by repertoire cloning of bone marrow mRNAs from an immune chimpanzee and analyzed for antigen binding specificity. The $V_H$ and $V_L$ sequences and neutralizing activity against the cytotoxicity of the anthrax toxin in vitro of Fabs were analyzed. Two monoclonal antibodies shared an identical HCDR3 sequence. Both Fabs neutralized the cytotoxicity of the anthrax toxin. The neutralizing antibodies were found to have very high binding affinity to PA with a Kd of $4\text{-}5 \times 10^{-11}$ M, which is 20-100 fold higher than the binding of receptor to PA. The binding epitope was located at aa 614-735, the site for binding to the cellular receptor (Petosa et al. 1997 *Nature* 385:833-838, 1997). A Fab was converted to full-length IgG1 by combining it with human sequences. In vivo rat protection assay showed that both anti-PA W1 and W2 protected rats from toxin challenge. In vitro studies revealed that the mechanism of protection afforded by both antibodies is inhibition of binding of PA to the cellular receptor. The full-length IgG1 is predicted to be invaluable for prophylactic and therapeutic application against anthrax in humans.

Definitions

As used herein, the term "antibody" means an immunoglobulin molecule or a fragment of an immunoglobulin molecule having the ability to specifically bind to a particular antigen. Antibodies are well known to those of ordinary skill in the science of immunology. As used herein, the term "antibody" means not only full-length antibody molecules but also fragments of antibody molecules retaining antigen binding ability. Such fragments are also well known in the art and are regularly employed both in vitro and in vivo. In particular, as used herein, the term "antibody" means not only full-length immunoglobulin molecules but also antigen binding active fragments such as the well-known active fragments F(ab')$_2$, Fab, Fv, and Fd.

As used herein, the term "anthrax" means any disease caused, directly or indirectly, by infection with *Bacillus anthracis*. Inhalation: Initial symptoms may resemble a common cold—sore throat, mild fever, muscle aches and malaise. After several days, the symptoms may progress to severe breathing problems and shock. Inhalation anthrax is usually fatal. Cutaneous: Anthrax infections can occur when the bacterium enters a cut or abrasion on the skin, such as when handling contaminated wool, hides, leather or hair products (especially goat hair) of infected animals. Skin infection begins as a raised itchy bump that resembles an insect bite but within 1-2 days develops into a vesicle and then a painless ulcer, usually 1-3 cm in diameter, with a characteristic black necrotic (dying) area in the center. Lymph glands in the adjacent area may swell. About 20% of untreated cases of cutaneous anthrax will result in death. Gastrointestinal: The intestinal disease form of anthrax may follow the consumption of contaminated meat and is characterized by an acute inflammation of the intestinal tract. Initial signs of nausea, loss of appetite, vomiting, fever are followed by abdominal pain, vomiting of blood, and severe diarrhea. Intestinal anthrax results in death in 25% to 60% of cases.

As used herein with respect to polypeptides, the term "substantially pure" means that the polypeptides are essentially free of other substances with which they may be found in nature or in vivo systems to an extent practical and appropriate for their intended use. In particular, the polypeptides are sufficiently pure and are sufficiently free from other biological constituents of their hosts cells so as to be useful in, for example, generating antibodies, sequencing, or producing pharmaceutical preparations. By techniques well known in the art, substantially pure polypeptides may be produced in light of the nucleic acid and amino acid sequences disclosed herein. Because a substantially purified polypeptide of the invention may be admixed with a pharmaceutically acceptable carrier in a pharmaceutical preparation, the polypeptide may comprise only a certain percentage by weight of the preparation. The polypeptide is nonetheless substantially pure in that it has been substantially separated from the substances with which it may be associated in living systems.

As used herein with respect to nucleic acids, the term "isolated" means: (1) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Regulatory sequences may also include enhancer sequences or upstream activator sequences, as desired.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification and selection of cells which have been transformed or transfected with the vector. Markers include, for example, genes encoding proteins which increase or decrease either resistance or sensitivity to antibiotics or other compounds, genes which encode enzymes whose activities are detectable by standard assays known in the art (e.g., B-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

Novel Anti-Anthrax PA Monoclonal Antibodies

The present invention derives, in part, from the isolation and characterization of a first and second novel chimpanzee Fab fragment and its humanized monoclonal antibody that selectively binds anthrax protective antigen and that we have designated anti-anthrax PAw 1 and PAw 1, respectively. Additionally, these new monoclonal antibodies have been shown to neutralize the cytotoxicity of the anthrax toxin. The paratope of the anti-anthrax PAw 1 and PAw 2 Fab fragment associated with the neutralization epitope on the anthrax PA is defined by the amino acid (aa) sequences of the immunoglobulin heavy and light chain V-regions depicted in FIG. 1 and, for PAw 1, SEQ ID NO: 1 and SEQ ID NO: 9, and for PAw 2, SEQ ID NO: 17 and SEQ ID NO: 25. The nucleic acid sequences coding for these aa sequences were identified by sequencing the Fab heavy chain and light chain fragments. Due to the degeneracy of the DNA code, the paratope is more properly defined by the derived aa sequences depicted in FIG. 1 and, for Anti-PAw 1, SEQ ID NO: 1 and SEQ ID NO: 9, and for Anti-PAw 2, SEQ ID NO: 17 and SEQ ID NO: 25.

In one set of embodiments, the present invention provides the full-length, humanized monoclonal antibody of the anti-anthrax PAw 1 antibody, or the anti-anthrax PAw 2 antibody or other anti-anthrax PA antibody in isolated form and in pharmaceutical preparations. Similarly, as described herein, the present invention provides isolated nucleic acids, host cells transformed with nucleic acids, and pharmaceutical preparations including isolated nucleic acids, encoding the full-length, humanized monoclonal antibody of the anti-anthrax PAw 1 antibody, or the anti-anthrax PAw 2 antibody or other anti-anthrax PA antibody. Finally, the present invention provides methods, as described more fully herein, employing these antibodies and nucleic acids in the in vitro and in vivo diagnosis, prevention and therapy of anthrax disease.

Significantly, as is well-known in the art, only a small portion of an antibody molecule, the paratope, is involved in the binding of the antibody to its epitope (see, in general, Clark, W. R. 1986 *The Experimental Foundations of Modern Immunology* Wiley & Sons, Inc., New York; Roitt, I. 1991 *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of a full-length antibody. Similarly, an antibody from which the Fc region has been enzymatically cleaved, or which has been produced without the Fc region, designated an Fab fragment, retains one of the antigen binding sites of a full-length antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986, supra; Roitt, 1991, supra). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

The complete amino acid sequences of the antigen-binding Fab portion of the anti-anthrax PAw 1 monoclonal antibody as well as the relevant FR and CDR regions are disclosed herein. SEQ ID NO: 1 discloses the amino acid sequence of the Fd fragment of anti-anthrax PAw 1. The amino acid sequences of the heavy chain FR1, CDR1, FR2, CDR2, FR3, CDR3 and FR4 regions are disclosed as SEQ ID NO: 2 through SEQ ID NO: 8, respectively. SEQ ID NO: 9 discloses the amino acid sequence of the light chain of anti-anthrax PAw 1. The amino acid sequences of the light chain FR1, CDR1, FR2, CDR2, FR3, CDR3 and FR4 regions are disclosed as SEQ ID NO: 10 through SEQ ID NO: 16, respectively.

The complete amino acid sequences of the antigen-binding Fab portion of the anti-anthrax PAw 2 monoclonal antibody as well as the relevant FR and CDR regions are disclosed herein. SEQ ID NO: 17 discloses the amino acid sequence of the Fd fragment of anti-anthrax PAw 2. The amino acid sequences of the heavy chain FR1, CDR1, FR2, CDR2, FR3, CDR3 and FR4 regions are disclosed as SEQ ID NO: 18 through SEQ ID NO: 24, respectively. SEQ ID NO: 25 discloses the amino acid sequence of the light chain of anti-anthrax PAw 2. The amino acid sequences of the light chain FR1, CDR1, FR2, CDR2, FR3, CDR3 and FR4 regions are disclosed as SEQ ID NO: 26 through SEQ ID NO: 32, respectively.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of full-length antibodies with antigen-binding ability, are often referred to as "chimeric" antibodies.

Thus, as will be apparent to one of ordinary skill in the art, the present invention also provides for F(ab')$_2$, Fab, Fv and Fd fragments of the anti-anthrax PAw 1 antibody, or the anti-anthrax PAw 2 antibody or other anti-anthrax PA antibody; chimeric antibodies in which the Fc and/or FR and/or CDR1 and/or CDR2 and/or light chain CDR3 regions of the anti-anthrax PAw 1 antibody, or the anti-anthrax PAw 2 antibody or other anti-anthrax PA antibody, have been replaced by homologous human or non-human sequences; chimeric F(ab')$_2$ fragment antibodies in which the FR and/or CDR1 and/or CDR2 and/or light chain CDR3 regions of the anti-anthrax PAw 1 antibody, or the anti-anthrax PAw 2 antibody or other anti-anthrax PA antibody, have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. Thus, those skilled in the art may alter the anti-anthrax PAw 1 antibody, or the anti-anthrax PAw 2 antibody or other anti-anthrax PA antibody, by the construction of CDR grafted or chimeric antibodies or antibody fragments containing all, or part thereof, of the disclosed heavy and light chain V-region CDR aa sequences (Jones, P. T. et al. 1986 *Nature* 321:522; Verhoeyen, M. et al. 1988 *Science* 39:1534; and Tempest, P. R. et al. 1991 *Bio/Technology* 9:266), without destroying the specificity of the antibodies for the anthrax PA epitope. Such CDR grafted or chimeric antibodies or antibody fragments can be effective in prevention and treatment of anthrax infection in animals (e.g. cattle) and man.

In preferred embodiments, the chimeric antibodies of the invention are fully human or humanized chimpanzee monoclonal antibodies including at least the heavy chain CDR3 region of the anti-anthrax PAw 1 antibody, or the anti-anthrax PAw 2 antibody or other anti-anthrax PA antibody. As noted above, such chimeric antibodies may be produced in which some or all of the FR regions of the anti-anthrax PAw 1 antibody, or the anti-anthrax PAw 2 antibody or other anti-anthrax PA antibody, have been replaced by other homologous human FR regions. In addition, the Fc portions may be replaced so as to produce IgA or IgM as well as IgG antibodies bearing some or all of the CDRs of the anti-anthrax PAw 1 antibody, or the anti-anthrax PAw 2 antibody or other anti-anthrax PA antibody. Of particular importance is the inclusion of the heavy chain CDR3 region and, to a lesser extent, the other CDRs of the anti-anthrax PAw 1 antibody, or the anti-anthrax PAw 2 antibody or other anti-anthrax PA antibody. Such fully human or humanized chimpanzee monoclonal antibodies will have particular utility in that they will not evoke an immune response against the antibody itself.

It is also possible, in accordance with the present invention, to produce chimeric antibodies including non-human sequences. Thus, one may use, for example, murine, ovine, equine, bovine or other mammalian Fc or FR sequences to replace some or all of the Fc or FR regions of the anti-anthrax PAw 1 antibody, or the anti-anthrax PAw 2 antibody or other anti-anthrax PA antibody. Some of the CDRs may be replaced as well. Again, however, it is preferred that at least the heavy chain CDR3 of the anti-anthrax PAw 1 antibody, or the anti-anthrax PAw 2 antibody or other anti-anthrax PA antibody, be included in such chimeric antibodies and, to a lesser extent, it is also preferred that some or all of the other CDRs of the anti-anthrax PAw 1 antibody, or the anti-anthrax PAw 2 antibody or other anti-anthrax PA antibody, be included. Such chimeric antibodies bearing non-human immunoglobulin sequences admixed with the CDRs of the anti-anthrax PAw 1 antibody, or the anti-anthrax PAw 2 antibody or other anti-anthrax PA antibody, are not preferred for use in humans and are particularly not preferred for extended use because they may evoke an immune response against the non-human sequences. They may, of course, be used for brief periods or in immunosuppressed individuals but, again, fully human or humanized chimpanzee monoclonal antibodies are preferred. Because such antibodies may be used for brief periods or in immunosuppressed subjects, chimeric antibodies bearing non-human mammalian Fc and FR sequences but including at least the heavy chain CDR3 of the anti-anthrax PAw 1 antibody, or the anti-anthrax PAw 2 antibody or other anti-anthrax PA antibody, are contemplated as alternative embodiments of the present invention.

For inoculation or prophylactic uses, the antibodies of the present invention are preferably full-length antibody molecules including the Fc region. Such full-length antibodies will have longer half-lives than smaller fragment antibodies (e.g. Fab) and are more suitable for intravenous, intraperitoneal, intramuscular, intracavity, subcutaneous, or transdermal administration.

In some embodiments, Fab fragments, including chimeric Fab fragments, are preferred. Fabs offer several advantages over F(ab')$_2$ and whole immunoglobulin molecules for this therapeutic modality. First, because Fabs have only one binding site for their cognate antigen, the formation of immune complexes is precluded whereas such complexes can be generated when bivalent F(ab')$_2$ and whole immunoglobulin molecules encounter their target antigen. This is of some importance because immune complex deposition in tissues can produce adverse inflammatory reactions. Second, because Fabs lack an Fc region they cannot trigger adverse inflammatory reactions that are activated by Fc, such as activation of the complement cascade. Third, the tissue penetration of the small Fab molecule is likely to be much better than that of the larger whole antibody. Fourth, Fabs can be produced easily and inexpensively in bacteria, such as *E. coli*, whereas whole immunoglobulin antibody molecules require mammalian cells for their production in useful amounts. The latter entails transfection of immunoglobulin sequences into mammalian cells with resultant transformation. Amplification of these sequences must then be achieved by rigorous selective procedures and stable transformants must be identified and maintained. The whole immunoglobulin molecules must be produced by stably transformed, high expression mammalian cells in culture with the attendant problems of serum-containing culture medium. In contrast, production of Fabs in *E. coli* eliminates these difficulties and makes it possible to produce these antibody fragments in large fermenters which are less expensive than cell culture-derived products.

In addition to Fabs, smaller antibody fragments and epitope-binding peptides having binding specificity for the epitope defined by the anti-anthrax PAw 1 antibody, or the anti-anthrax PAw 2 antibody or other anti-anthrax PA antibody, are also contemplated by the present invention and can also be used to bind or neutralize the toxin. For example, single chain antibodies can be constructed according to the method of U.S. Pat. No. 4,946,778, to Ladner et al. Single chain antibodies comprise the variable regions of the light and heavy chains joined by a flexible linker moiety. Yet smaller is the antibody fragment known as the single domain antibody or Fd, which comprises an isolated VH single domain. Techniques for obtaining a single domain antibody with at least some of the binding specificity of the full-length antibody from which they are derived are known in the art.

It is possible to determine, without undue experimentation, if an altered or chimeric antibody has the same specificity as the anti-anthrax PAw 1 antibody, or the anti-anthrax PAw 2 antibody or other anti-anthrax PA antibody, of the invention by ascertaining whether the former blocks the latter from binding to anthrax PA. If the monoclonal antibody being tested competes with the anti-anthrax PAw 1 antibody, or the anti-anthrax PAw 2 antibody or other anti-anthrax PA antibody, as shown by a decrease in binding of the anti-anthrax PAw 1 antibody, or the anti-anthrax PAw 2 antibody or other anti-anthrax PA antibody, then it is likely that the two monoclonal antibodies bind to the same, or a closely spaced, epitope. Still another way to determine whether a monoclonal antibody has the specificity of the anti-anthrax PAw 1 antibody, or the anti-anthrax PAw 2 antibody or other anti-anthrax PA antibody, of the invention is to pre-incubate the anti-anthrax PAw 1 antibody, or the anti-anthrax PAw 2 antibody or other anti-anthrax PA antibody, with anthrax PA with which it is normally reactive, and then add the monoclonal antibody being tested to determine if the monoclonal antibody being tested is inhibited in its ability to bind anthrax PA. If the monoclonal antibody being tested is inhibited then, in all likelihood, it has the same, or a functionally equivalent, epitope and specificity as the anti-anthrax PAw 1 antibody, or the anti-anthrax PAw 2 antibody or other anti-anthrax PA antibody, of the invention. Screening of monoclonal antibodies of the invention also can be carried out utilizing anthrax toxin and determining whether the monoclonal antibody neutralizes cytotoxicity of the anthrax toxin.

By using the antibodies of the invention, it is now possible to produce anti-idiotypic antibodies which can be used to screen other monoclonal antibodies to identify whether the antibody has the same binding specificity as an antibody of the invention. In addition, such antiidiotypic antibodies can be used for active immunization (Herlyn, D. et al. 1986 *Science* 232:100). Such anti-idiotypic antibodies can be produced using well-known hybridoma techniques (Kohler, G. and Milstein, C. 1975 *Nature* 256:495). An anti-idiotypic antibody is an antibody which recognizes unique determinants present on the monoclonal antibody produced by the cell line of interest. These determinants are located in the hypervariable region of the antibody. It is this region which binds to a given epitope and, thus, is responsible for the specificity of the antibody.

An anti-idiotypic antibody can be prepared by immunizing an animal with the monoclonal antibody of interest. The immunized animal will recognize and respond to the idiotypic determinants of the immunizing antibody and produce an antibody to these idiotypic determinants. By using the anti-idiotypic antibodies of the immunized animal, which are specific for the monoclonal antibodies of the invention, it is possible to identify other clones with the same idiotype as the antibody of the hybridoma used for immunization. Idiotypic identity between monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the image of the epitope bound by the first monoclonal antibody. Thus, the anti-idiotypic monoclonal antibody can be used for immunization, since the anti-idiotype monoclonal antibody binding domain effectively acts as an antigen.

Nucleic Acids Encoding Anti-Anthrax PA Antibodies

Given the disclosure herein of the amino acid sequences of the heavy chain Fd and light chain variable domains of the anti-anthrax PAw 1 antibody, or the anti-anthrax PAw 2 antibody or other anti-anthrax PA antibody, one of ordinary skill in the art is now enabled to produce nucleic acids which encode this antibody or which encode the various fragment antibodies or chimeric antibodies described above. It is contemplated that such nucleic acids will be operably joined to other nucleic acids forming a recombinant vector for cloning or for expression of the antibodies of the invention. The present invention includes any recombinant vector containing the coding sequences, or part thereof, whether for prokaryotic or eukaryotic transformation, transfection or gene therapy. Such vectors may be prepared using conventional molecular biology techniques, known to those with skill in the art, and would comprise DNA coding sequences for the immunoglobulin V-regions of the anti-anthrax PAw 1 antibody, or the anti-anthrax PAw 2 antibody or other anti-anthrax PA antibody, including framework and CDRs or parts thereof, and a suitable promoter either with (Whittle, N. et al. 1987 *Protein Eng.* 1:499 and Burton, D. R. et al. 1994 *Science* 266:1024) or without (Marasco, W. A. et al. 1993 *PNAS USA* 90:7889 and Duan, L. et al. 1994 *PNAS USA* 91:5075) a signal sequence for export or secretion. Such vectors may be transformed or transfected into prokaryotic (Huse, W. D. et al. 1989 *Science* 246:1275; Ward, S. et al. 1989 *Nature* 341:544; Marks, J. D. et al. 1991 *J Mol Biol* 222:581; and Barbas, C. F. et al. 1991 *PNAS USA* 88:7987) or eukaryotic (Whittle, N. et al. 1987 *Protein Eng* 1:499 and Burton, D. R. et al. 1994 *Science* 266:1024) cells or used for gene therapy (Marasco, W. A. et al. 1993 *PNAS USA* 90:7889 and Duan, L. et al. 1994 *PNAS USA* 91:5075) by conventional techniques, known to those with skill in the art.

The expression vectors of the present invention include regulatory sequences operably joined to a nucleotide sequence encoding one of the antibodies of the invention. As used herein, the term "regulatory sequences" means nucleotide sequences which are necessary for or conducive to the transcription of a nucleotide sequence which encodes a desired polypeptide and/or which are necessary for or conducive to the translation of the resulting transcript into the desired polypeptide. Regulatory sequences include, but are not limited to, 5' sequences such as operators, promoters and ribosome binding sequences, and 3' sequences such as polyadenylation signals. The vectors of the invention may optionally include 5' leader or signal sequences, 5' or 3' sequences encoding fusion products to aid in protein purification, and various markers which aid in the identification or selection of transformants. The choice and design of an appropriate vector is within the ability and discretion of one of ordinary skill in the art. The subsequent purification of the antibodies may be accomplished by any of a variety of standard means known in the art.

A preferred vector for screening monoclonal antibodies, but not necessarily preferred for the mass production of the antibodies of the invention, is a recombinant DNA molecule containing a nucleotide sequence that codes for and is capable of expressing a fusion polypeptide containing, in the direction of amino- to carboxy-terminus, (1) a prokaryotic secretion signal domain, (2) a polypeptide of the invention, and, optionally, (3) a fusion protein domain. The vector includes DNA regulatory sequences for expressing the fusion polypeptide, preferably prokaryotic, regulatory sequences. Such vectors can be constructed by those with skill in the art and have been described by Smith, G. P. et al. (1985 *Science* 228:1315; Clackson, T. et al. 1991 *Nature* 352:624; Kang et al. 1991 in: *Methods: A Companion to Methods in Enzymology: Vol.* 2, R. A. Lerner and D. R. Burton, eds. Academic Press, NY, pp 111-118; Barbas, C. F. et al. 1991 *PNAS USA* 88:7978; Roberts, B. L. et al. 1992 *PNAS USA* 89:2429).

A fusion polypeptide may be useful for purification of the antibodies of the invention. The fusion domain may, for example, include a poly-His tail which allows for purification on Ni+ columns or the maltose binding protein of the commercially available vector pMAL (New England BioLabs, Beverly, Mass.). A currently preferred, but by no means necessary, fusion domain is a filamentous phage membrane anchor. This domain is particularly useful for screening phage display libraries of monoclonal antibodies but may be of less utility for the mass production of antibodies. The filamentous phage membrane anchor is preferably a domain of the cpIII or cpVIII coat protein capable of associating with the matrix of a filamentous phage particle, thereby incorporating the fusion polypeptide onto the phage surface, to enable solid phase binding to specific antigens or epitopes and thereby allow enrichment and selection of the specific antibodies or fragments encoded by the phagemid vector.

The secretion signal is a leader peptide domain of a protein that targets the protein to the membrane of the host cell, such as the periplasmic membrane of Gram-negative bacteria. A preferred secretion signal for *E. coli* is a pelB secretion signal. The leader sequence of the pelB protein has previously been used as a secretion signal for fusion proteins (Better, M. et al. 1988 *Science* 240:1041; Sastry, L. et al. 1989 *PNAS USA* 86:5728; and Mullinax, R. L. et al., 1990 *PNAS USA* 87:8095). Amino acid residue sequences for other secretion signal polypeptide domains from *E. coli* useful in this invention can be found in Neidhard, F. C. (ed.), 1987 *Escherichia coli* and *Salmonella Typhimurium: Typhimurium Cellular and Molecular Biology*, American Society for Microbiology, Washington, D.C.

To achieve high levels of gene expression in *E. coli*, it is necessary to use not only strong promoters to generate large quantities of mRNA, but also ribosome binding sites to ensure that the mRNA is efficiently translated. In *E. coli*, the ribosome binding site includes an initiation codon (AUG) and a sequence 3-9 nucleotides long located 3-11 nucleotides upstream from the initiation codon (Shine et al. 1975 *Nature* 254:34). The sequence, which is called the Shine-Dalgarno (SD) sequence, is complementary to the 3' end of *E. coli* 16S rRNA. Binding of the ribosome to mRNA and the sequence at the 3' end of the mRNA can be affected by several factors: the degree of complementarity between the SD sequence and 3' end of the 16S rRNA; the spacing lying between the SD sequence and the AUG; and the nucleotide sequence following the AUG, which affects ribosome binding. The 3' regulatory sequences define at least one termination (stop) codon in frame with and operably joined to the heterologous fusion polypeptide.

In preferred embodiments with a prokaryotic expression host, the vector utilized includes a prokaryotic origin of replication or replicon, i.e., a DNA sequence having the ability to direct autonomous replication and maintenance of the recombinant DNA molecule extrachromosomally in a prokaryotic host cell, such as a bacterial host cell, transformed therewith. Such origins of replication are well known in the art. Preferred origins of replication are those that are efficient in the host organism. A preferred host cell is *E. coli*. For use of a vector in *E. coli*, a preferred origin of replication is ColEI found in pBR322 and a variety of other common plasmids. Also preferred is the p15A origin of replication found on pACYC and its derivatives. The ColEI and p15A replicons have been extensively utilized in molecular biology, are available on a variety of plasmids and are described by Sambrook. et al. 1989 *Molecular Cloning: A Laboratory Manual*, 2nd edition, Cold Spring Harbor Laboratory Press.

In addition, those embodiments that include a prokaryotic replicon preferably also include a gene whose expression confers a selective advantage, such as drug resistance, to a bacterial host transformed therewith. Typical bacterial drug resistance genes are those that confer resistance to ampicillin, tetracycline, neomycin/kanamycin or chloramphenicol.

Vectors typically also contain convenient restriction sites for insertion of translatable DNA sequences. Exemplary vectors are the plasmids pUC18 and pUC19 and derived vectors such as those commercially available from suppliers such as Invitrogen, (San Diego, Calif.).

When the antibodies of the invention include both heavy chain and light chain sequences, these sequences may be encoded on separate vectors or, more conveniently, may be expressed by a single vector. The heavy and light chain may, after translation or after secretion, form the heterodimeric structure of natural antibody molecules. Such a heterodimeric antibody may or may not be stabilized by disulfide bonds between the heavy and light chains.

A vector for expression of heterodimeric antibodies, such as the full-length antibodies of the invention or the $F(ab')_2$, Fab or Fv fragment antibodies of the invention, is a recombinant DNA molecule adapted for receiving and expressing translatable first and second DNA sequences. That is, a DNA expression vector for expressing a heterodimeric antibody provides a system for independently cloning (inserting) the two translatable DNA sequences into two separate cassettes present in the vector, to form two separate cistrons for expressing the first and second polypeptides of a heterodimeric antibody. The DNA expression vector for expressing two cistrons is referred to as a di-cistronic expression vector.

Preferably, the vector comprises a first cassette that includes upstream and downstream DNA regulatory sequences operably joined via a sequence of nucleotides adapted for directional ligation to an insert DNA. The upstream translatable sequence preferably encodes the secretion signal as described above. The cassette includes DNA regulatory sequences for expressing the first antibody polypeptide that is produced when an insert translatable DNA sequence (insert DNA) is directionally inserted into the cassette via the sequence of nucleotides adapted for directional ligation.

The dicistronic expression vector also contains a second cassette for expressing the second antibody polypeptide. The second cassette includes a second translatable DNA sequence that preferably encodes a secretion signal, as described above, operably joined at its 3' terminus via a sequence of nucleotides adapted for directional ligation to a downstream DNA sequence of the vector that typically defines at least one stop codon in the reading frame of the cassette. The second translatable DNA sequence is operably joined at its 5' terminus to DNA regulatory sequences forming the 5' elements. The second cassette is capable, upon insertion of a translatable DNA sequence (insert DNA), of expressing the second fusion polypeptide comprising a secretion signal with a polypeptide coded by the insert DNA.

The antibodies of the present invention may additionally, of course, be produced by eukaryotic cells such as CHO cells, human or mouse hybridomas, immortalized B-lymphoblastoid cells, and the like. In this case, a vector is constructed in which eukaryotic regulatory sequences are operably joined to the nucleotide sequences encoding the antibody polypeptide or polypeptides. The design and selection of an appropriate eukaryotic vector is within the ability and discretion of one of ordinary skill in the art. The subsequent purification of the antibodies may be accomplished by any of a variety of standard means known in the art.

The antibodies of the present invention may furthermore, of course, be produced in plants. In 1989, Hiatt et al. (1989 *Nature* 342:76) first demonstrated that functional antibodies could be produced in transgenic plants. Since then, a considerable amount of effort has been invested in developing plants for antibody (or "plantibody") production (for reviews see Giddings G. et al. 2000 *Nat Biotechnol* 18:1151; Fischer R. and Emans N. 2000 *Transgenic Res* 9:279). Recombinant antibodies can be targeted to seeds, tubers, or fruits, making administration of antibodies in such plant tissues advantageous for immunization programs in developing countries and worldwide.

In another embodiment, the present invention provides host cells, both prokaryotic and eukaryotic, transformed or transfected with, and therefore including, the vectors of the present invention.

Diagnostic and Pharmaceutical Anti-Anthrax PA Antibody Preparations

The invention also relates to a method for preparing diagnostic or pharmaceutical compositions comprising the monoclonal antibodies of the invention or polynucleotide sequences encoding the antibodies of the invention or part thereof, the pharmaceutical compositions being used for immunoprophylaxis or immunotherapy of anthrax disease. The pharmaceutical preparation includes a pharmaceutically acceptable carrier. Such carriers, as used herein, means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

A preferred embodiment of the invention relates to monoclonal antibodies whose heavy chains comprise in CDR3 the polypeptide having SEQ ID NO: 7, and/or whose light chains comprise in CDR3 the polypeptide having SEQ ID NO: 15; whose heavy chains comprise in CDR3 the polypeptide having SEQ ID NO: 23, and/or whose light chains comprise in CDR3 the polypeptide having SEQ ID NO: 31; and conservative variations of these peptides. Also encompassed by the present invention are certain amino acid sequences that bind to epitopic sequences in domain 4 of anthrax PA corresponding to aa 614-735 and that confer neutralization of anthrax toxin when bound thereto. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies having the substituted polypeptide also bind or neutralize anthrax PA. Analogously, another preferred embodiment of the invention relates to polynucleotides which encode the above noted heavy chain polypeptides and to polynucleotide sequences which are complementary to these polynucleotide sequences. Complementary polynucleotide sequences include those sequences that hybridize to the polynucleotide sequences of the invention under stringent hybridization conditions.

The anti-anthrax PA antibodies of the invention may be labeled by a variety of means for use in diagnostic and/or pharmaceutical applications. There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibodies of the invention, or will be able to ascertain such, using routine experimentation. Furthermore, the binding of these labels to the monoclonal antibodies of the invention can be done using standard techniques common to those of ordinary skill in the art.

Another labeling technique which may result in greater sensitivity consists of coupling the antibodies to low molecular weight haptens. These haptens can then be specifically altered by means of a second reaction. For example, it is common to use haptens such as biotin, which reacts with avidin, or dinitrophenol, pyridoxal, or fluorescein, which can react with specific antihapten antibodies.

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a monoclonal antibody of the invention that is, or can be, detectably labeled. The kit may also have containers containing buffer(s) and/or a container comprising a reporter-means, such as a biotin-binding protein, such as avidin or streptavidin, bound to a reporter molecule, such as an enzymatic or fluorescent label.

In Vitro Detection and Diagnostics

The monoclonal antibodies of the invention are suited for in vitro use, for example, in immunoassays in which they can be utilized in liquid phase or bound to a solid phase carrier. In addition, the monoclonal antibodies in these immunoassays can be detectably labeled in various ways. Examples of types of immunoassays which can utilize the monoclonal antibodies of the invention are competitive and non-competitive immunoassays in either a direct or indirect format. Examples of such immunoassays are the radioimmunoassay (RIA) and the sandwich (immunometric) assay. Detection of antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The monoclonal antibodies of the invention can be bound to many different carriers and used to detect the presence of anthrax PA. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble for purposes of the invention. Those skilled in the art will know of other suitable carriers for binding monoclonal antibodies, or will be able to ascertain such, using routine experimentation.

For purposes of the invention, anthrax PA may be detected by the monoclonal antibodies of the invention when present in biological fluids and tissues. Any sample containing a detectable amount of anthrax PA can be used. A sample can be a liquid such as urine, saliva, cerebrospinal fluid, blood, serum or the like; a solid or semi-solid such as tissues, feces, or the like; or, alternatively, a solid tissue such as those commonly used in histological diagnosis.

In Vivo Detection of Anthrax PA

In using the monoclonal antibodies of the invention for the in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having the anthrax PA antigen for which the monoclonal antibodies are specific.

The concentration of detectably labeled monoclonal antibody which is administered should be sufficient such that the binding to anthrax PA is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. The dosage of monoclonal antibody can vary from about 0.01 mg/kg to about 50 mg/kg, preferably 0.1 mg/kg to about 20 mg/kg, most preferably about 0.1 mg/kg to about 2 mg/kg. Such dosages may vary, for example, depending on whether multiple injections are given, on the tissue being assayed, and other factors known to those of skill in the art.

For in vivo diagnostic imaging, the type of detection instrument available is a major factor in selecting an appropriate radioisotope. The radioisotope chosen must have a type of decay which is detectable for the given type of instrument. Still another important factor in selecting a radioisotope for in vivo diagnosis is that the half-life of the radioisotope be long enough such that it is still detectable at the time of maximum uptake by the target, but short enough such that deleterious radiation with respect to the host is acceptable. Ideally, a radioisotope used for in vivo imaging will lack a particle emission but produce a large number of photons in the 140-250 keV range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions are the bifunctional chelating agents such as diethylenetriaminepentacetic acid (DTPA) and ethylenediaminetetra-acetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr and $^{56}$Fe.

The monoclonal antibodies of the invention can be used in vitro and in vivo to monitor the course of anthrax disease therapy. Thus, for example, by measuring the increase or decrease in the number of cells infected with anthrax or changes in the concentration of anthrax PA present in the body or in various body fluids, it would be possible to determine whether a particular therapeutic regimen aimed at ameliorating anthrax disease is effective.

Prophylaxis and Therapy of Anthrax Disease

The monoclonal antibodies can also be used in prophylaxis and as therapy for anthrax disease in humans. The terms, "prophylaxis" and "therapy" as used herein in conjunction with the monoclonal antibodies of the invention denote both prophylactic as well as therapeutic administration and both passive immunization with substantially purified polypeptide products, as well as gene therapy by transfer of polynucleotide sequences encoding the product or part thereof. Thus, the monoclonal antibodies can be administered to high-risk subjects in order to lessen the likelihood and/or severity of anthrax disease or administered to subjects already evidencing active anthrax infection. In the present invention, Fab fragments also bind or neutralize anthrax PA and therefore may be used to treat anthrax infection but full-length antibody molecules are otherwise preferred.

As used herein, a "prophylactically effective amount" of the monoclonal antibodies of the invention is a dosage large enough to produce the desired effect in the protection of individuals against anthrax infection for a reasonable period of time, such as one to two months or longer following administration. A prophylactically effective amount is not, however, a dosage so large as to cause adverse side effects, such as hyperviscosity syndromes, pulmonary edema, congestive heart failure, and the like. Generally, a prophylactically effective amount may vary with the subject's age, condition, and sex, as well as the extent of the disease in the subject and can be determined by one of skill in the art. The dosage of the prophylactically effective amount may be adjusted by the individual physician or veterinarian in the event of any complication. A prophylactically effective amount may vary from about 0.01 mg/kg to about 50 mg/kg, preferably from about 0.1 mg/kg to about 20 mg/kg, most preferably from about 0.2 mg/kg to about 2 mg/kg, in one or more administrations (priming and boosting).

As used herein, a "therapeutically effective amount" of the monoclonal antibodies of the invention is a dosage large enough to produce the desired effect in which the symptoms of anthrax disease are ameliorated or the likelihood of infection is decreased. A therapeutically effective amount is not, however, a dosage so large as to cause adverse side effects, such as hyperviscosity syndromes, pulmonary edema, congestive heart failure, and the like. Generally, a therapeutically effective amount may vary with the subject's age, condition, and sex, as well as the extent of the disease in the subject and can be determined by one of skill in the art. The dosage of the therapeutically effective amount may be adjusted by the individual physician or veterinarian in the event of any complication. A therapeutically effective amount may vary from about 0.01 mg/kg to about 50 mg/kg, preferably from about 0.1 mg/kg to about 20 mg/kg, most preferably from about 0.2 mg/kg to about 2 mg/kg, in one or more dose administrations daily, for one or several days. Preferred is administration of the antibody for 2 to 5 or more consecutive days in order to avoid "rebound" of bacterial replication from occurring.

The monoclonal antibodies of the invention can be administered by injection or by gradual infusion over time. The administration of the monoclonal antibodies of the invention may, for example, be intravenous, intraperitoneal, intramuscular, intracavity, subcutaneous, or transdermal. Techniques for preparing injectate or infusate delivery systems containing antibodies are well known to those of skill in the art. Generally, such systems should utilize components which will not significantly impair the biological properties of the antibodies, such as the paratope binding capacity (see, for example, *Remington's Pharmaceutical Sciences*, 18*th* edition, 1990, Mack Publishing). Those of skill in the art can readily determine the various parameters and conditions for producing antibody injectates or infusates without resort to undue experimentation.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and the like.

Efficient Neutralization of Anthrax Toxin by Chimpanzee Monoclonal Antibodies Against Protective Antigen Four single-chain Fv (scFvs) against protective antigen (PA) and two against lethal factor (LF) of anthrax were isolated from a phage display library generated from immunized chimpanzees. Only two scFvs recognizing PA (W1 and W2) neutralized the cytotoxicity of lethal toxin in a macrophage lysis assay. Full-length IgGs of W1 and W2 efficiently protected rats from toxin challenge. The epitope recognized by W1 and W2 was conformational and formed by C-terminal amino acids 614-735 of PA. W1 and W2 each bound to PA with a $K_d$ of $4$-$5 \times 10^{-11}$ M, which is 20-100 fold higher affinity than that for the interaction of receptor and PA. W1 and W2 inhibited the binding of PA to the receptor, indicating that this was the mechanism of protection. These data indicate that the W1 and W2 chimpanzee MAbs are predicted to serve as PA entry-inhibitors for use in the emergency prophylaxis and treatment of anthrax.

Introduction

Anthrax has emerged as a serious bioterrorist threat. Inhalational anthrax is usually fatal if treatment is delayed (Jernigan J. A. et al. 2001 *Emerg Infect Dis* 7:933-44). The lethality of anthrax is primarily due to the effects of anthrax toxin, which has three components; a nontoxic, receptor-binding protein, protective antigen (PA), and two toxic, catalytic proteins, lethal factor (LF) and edema factor (EF). The entry of the toxins into the cell is initiated by rapid binding of the 83 kDa PA to the cellular receptor whereupon the bound PA is cleaved by a furin-like protease into an N-terminal 20 kDa protein, PA20, and a C-terminal 63 kDa protein, PA63 (Collier R. J. & Young J. A. 2003 *Annu Rev Cell Dev Biol* 19:45-70). The PA63 spontaneously oligomerizes into an antigenically distinct heptameric ring that can no longer be displaced from the cellular receptor. The heptamer binds up to three molecules of LF or EF. The resulting complexes enter the cell by endocytosis and a conformational change induced by low pH results in the release of bound LF and EF into the cytosol. Several steps in this process could be targets for antibodies; for example, antibodies to PA might block receptor binding, oligomerization, or binding of LF and EF, and antibodies to LF and EF might prevent their binding to PA.

Passive immunization with polyclonal antibodies protects laboratory animals from effects of anthrax toxins (Little S. F. et al. 1997 *Infect Immun* 65:5171-5; Kobiler D. et al. 2002 *Infect Immun* 70:544-60). Passive immunization of humans with anthrax neutralizing antibodies may provide an effective treatment when vaccination against anthrax is not practical or antibiotic treatment is not effective. Antibody therapy in conjunction with antibiotics would also be useful when the accumulated level of toxin would be detrimental even if further bacterial growth was inhibited. Recently, several recombinant monoclonal antibodies against PA were shown to protect animals from challenge with anthrax toxin (Maynard J. A. et al. 2002 *Nat Biotechnol* 20:597-601; Wild M. A. et al. 2003 *Nat Biotechnol* 21:1305-6; Sawada-Hirai R. et al. 2004 *J Immune Based Ther Vaccines* 2:5). Since chimpanzee immunoglobulins are virtually identical to those of humans (Schofield D. J. et al. 2002 *Virology* 292:127-36; Ehrlich P. H. et al. 1988 *Clin Chem* 34:1681-8; Ehrlich P. H. et al. 1990 *Hum Antibodies Hybridomas* 1:23-6), high-affinity chimpanzee antibodies that neutralize anthrax toxins should have therapeutic value comparable to that of human antibodies. Here, we report the identification and characterization of potent neutralizing chimpanzee monoclonal antibodies against PA.

Materials and Methods

Reagents.

Recombinant PA, PA63, LF and EF were obtained from List Biologicals (Campbell, Calif.) or made in our laboratory. Enzymes used in molecular cloning were purchased from New England BioLabs (Beverly, Mass.). Oligonucleotides were synthesized by Invitrogen (Carlsbad, Calif.). Anti-His horseradish peroxidase (HRP) conjugate, anti-human Fab HRP conjugate and anti-human Fc agarose were purchased from Sigma (St. Louis, Mo.). Nickel-agarose beads were from Invitrogen.

Animals.

Chimpanzees 1603 and 1609 were immunized three times, two weeks apart, with 50 μg each of recombinant PA, LF and EF with alum adjuvant. Bone marrow was aspirated from the iliac crest of these animals eight weeks after the last immunization. Fischer 344 rats were purchased from Taconic Farms (Germantown, N.Y.). All animal experiments were performed under protocols approved by the NIAID Animal Care and Use Committee.

Library Construction and Selection.

Lymphocytes from the bone marrow aspirate were isolated on a Ficoll gradient. mRNA was extracted from $10^8$ lymphocytes with an mRNA purification kit (Amersham Biosciences, Piscataway, N.J.). cDNA was synthesized with a first-strand cDNA synthesis kit from Amersham Biosciences. The VH and Vκ genes were amplified by PCR with 30 cycles of 95° C., 1 min, 58° C., 1 min, and 72° C. 1 min, using a mixture of primers for human V-genes described earlier (Sblattero D. & Bradbury A. A. 1998 *Immunotechnology* 3:271-8). The single-chain variable Fragment (scFv) was assembled from VH and Vκ via splicing by overlap extension PCR (SOE-PCR). The gel-purified scFv DNA was digested with SfiI and cloned into a pAK100 vector that also had been cut with SfiI (Krebber A. et al. 1997 *J Immunol Methods* 201:35-55).

The recombinant plasmids were transformed into *E. coli* XL1-blue (Stratagene, La Jolla, Calif.) by electroporation, resulting in a library of $5 \times 10^7$ individual clones. The phagemid production, panning and screening were essentially the same as described by Krebber et al. 1997 (Krebber A. et al. 1997 *J Immunol Methods* 201:35-55). In brief, the phagemids were rescued by superinfection with helper phage, VCS M13 (Stratagene), and subjected to panning on PA, LF and EF proteins coated on ELISA wells. Nonspecifically-adsorbed phages were removed by extensive washing. Specifically bound phages were eluted with 100 mM triethylamine, neutralized in pH, and amplified. After three rounds of panning, randomly picked single phage-scFv clones were screened for specific binding by phage ELISA (Harrison J. L. et al. 1996 *Methods Enzymol* 267:83-109). Clones that differentially bound to specific antigens with $A_{450}$ values of >1.0 were scored as positive, whereas values of <0.2 were scored as negative. For clones that bound specifically to PA, LF or EF, the variable region of heavy (VH) and light (VL) chain genes were sequenced, and their corresponding amino acid sequences were aligned.

Conversion of scFv to Fab and to Full-Length IgG.

To convert scFv to Fab, eight primers were designed as follows:

```
Fab H-5':
                                    (SEQ ID NO: 41)
ACCGTCTCCTCAGCCTCCACCAAGGGCCCATCGGT;

Fab H-3':
                                    (SEQ ID NO: 42)
AATGAGATCTGCGGCCGCTTAAATTAATTAAT;

Fab L-5':
                                    (SEQ ID NO: 43)
GTGGAAATCAAACGAACTGTGGCTGCACCATCTGT;

Fab L-3':
                                    (SEQ ID NO: 44)
AGGTATTTCATTTTAAATTCCTCCT;

PA H-5':
                                    (SEQ ID NO: 45)
GAGGTGCAGCTGCTCGAGACTGGAGGAGGCTT;

PA H-3':
                                    (SEQ ID NO: 46)
CTTGGTGGAGGCTGAGGAGACGGTGACCGTGGTCCCT;

PA L-5':
                                    (SEQ ID NO: 47)
TGGAGGTGGATCCGAGCTCGTAATGACGCAGTCT;

PA L-3':
                                    (SEQ ID NO: 48)
AGCCACAGTTCGTTTGATTTCCACCTTGGTCCCAGG.
```

First-strand cDNA of CH1 and Cκ gene fragments were synthesized from human spleen cell total RNA (BD Biosciences, Mountain View, Calif.) and amplified by PCR with primers of Fab H-5'/-3' and Fab L-5'/-3', respectively. The VH and Vκ gene fragments were amplified by PCR using anti-PA scFv DNA as a template and PA H-5'/-3' and PA L-5'/-3' as primers. The Fd (VH-CH1) and κ-chain segments (Vκ-Cκ) were produced through SOE-PCR of VH/CH1 and Vκ/Cκ, with PA H-5'/Fab H-3' and PA L-5'/Fab L-3' as primers. The Fd region was digested with XhoI and NotI and the κ-chain region with XbaI and SacI. The digested DNA fragments were cloned into pComb3H at the matching restriction sites (Glamann J. et al. 1998 *J Virol* 72:585-92).

The Fab was converted to full-length IgG by digestion of Fd with XhoI and ApaI and cloning into a pCDHC68b vector (Trill J. J. et al. 1995 *Curr Opin Biotechnol* 6:553-60) that contains human heavy chain constant region to yield plasmid pPAH. The κ-chain was digested with XbaI and SacI and cloned into a pCNHLC vector (Trill J. J. et al. 1995 *Curr Opin Biotechnol* 6:553-60) to yield plasmid pPAK.

Expression and Purification of scFv, Fab and IgG.

Both scFv and Fab were expressed in *E. coli*. Briefly, bacteria were cultured in 2×YT medium containing 2% glucose and appropriate antibiotics at 30° C. until the $OD_{600}$ was 0.5-1. The culture was diluted 5-fold in 2×YT without glucose and containing 0.2 mM IPTG and incubated at 27° C. for 20 h. The expressed proteins were purified by chromatography on nickel-charged affinity resins (Invitrogen).

Full-length IgG plasmids pPAH and pPAK that contained heavy-chain and light chain of anti-anthrax toxin components were co-transfected into 293T cells for transient expression. The IgG was purified by affinity chromatography on anti-human Fc agarose (Sigma).

The purity of each antibody was determined by SDS-polyacrylamide gel electrophoresis (SDS-PAGE) (Novex, Invitrogen) and the protein concentration was determined by BCA assay (Pierce Biotechnology, Rockford, Ill.) and ELISA with a purified human IgG (Jackson ImmunoResearch, West Grove, Pa.) as a standard.

ELISA Assay.

PA, LF and unrelated proteins (BSA, thyroglobulin, lysozyme, phosphorylase b) were coated onto a 96-well plate by placing 100 μl of protein at 5 μg/ml in carbonate buffer, pH 9.5, in each well and incubating the plate at room temperature overnight. Serial dilutions of soluble scFv, Fab, IgG or phage were added to the wells and plates were incubated for 2 h at room temperature (RT). The plates were washed and the secondary antibody conjugate (anti-His-HRP, anti-human Fab-HRP, or anti-M13-HRP) was added and incubated for 1 h at RT. The plates were washed and the color was developed by adding tetramethylbenzidine solution (TMB) (Sigma). The plates were read at $OD_{450}$ in an ELISA plate reader.

Competitive ELISA.

Recombinant PA at a concentration of 5 μg/ml in carbonate buffer, pH 9.5, was coated onto the wells of an ELISA plate. Wells were then incubated at room temperature with anti-PA W2 Fab at different concentrations for 1 h. Anti-PA W2 Fab was removed from the wells and mouse anti-PA MAbs 14B7 and 2D3 (Little S. F. et al. 1996 *Microbiology* 142 (Pt 3):707-15) respectively were added to the wells at 0.5 μg/ml. Plates were incubated for 1 h, washed and bound MAbs were detected by the addition of HRP-conjugated anti-mouse antibody followed by TMB substrate. The binding to PA by 14B7 and 2D3 was calculated by dividing the OD value in the absence of W2 with that in the presence of W2. Competition between W1 Fab vs. W2 IgG or W2 Fab vs. W1 IgG was tested as described above except that HRP-conjugated anti-human Fc was used as the secondary antibody.

Affinity Measurement.

Surface plasmon resonance (SPR) biosensor experiments were conducted with a Biacore 3000 instrument (Biacore, Piscataway, N.J.) using short carboxy-methylated dextran sensor surfaces (CM3, Biacore) and standard amine coupling as described in detail elsewhere (Schuck P. et al. In: *Current Protocols in Protein Science* Vol. 2., Coligan J E, Dunn B M, Ploegh H L, Speicher D W and Wingfield P T, eds. New York: John Wiley & Sons, 1999:20.2.1-20.2.21).

Experiments were conducted in two configurations: First, antibodies were immobilized to the surface and the kinetics of binding and dissociation of PA were recorded for 10 min and 2 h, respectively, at PA concentrations of 1, 10, 100, and 1,000 nM. In order to eliminate the effect of immobilization-induced surface site heterogeneity and mass transport limitation in the determination of the binding constants (Schuck P. 1997 *Ann Rev Biophys Biomol Struct* 26:541-566), the kinetic traces were globally fitted with a model for continuous ligand distributions (Svitel J. et al. 2003 *Biophys J* 84:4062-4077) combined with two-compartment approximation of mass transport. Second, solution competition experiments were conducted, in which soluble Fab at different concentrations was pre-incubated with PA for 24 h, and the concentration of unbound PA was determined from the initial slope of surface binding when passing the mixture over the antibody-functionalized surface. Standard competition isotherms were used for the analysis (Schuck P. et al. In: *Current Protocols in Protein Science* Vol. 2., Coligan J E, Dunn B M, Ploegh H L, Speicher D W and Wingfield P T, eds. New York: John Wiley & Sons, 1999:20.2.1-20.2.21; Schuck P. 1997 *Ann Rev Biophys Biomol Struct* 26:541-566).

Epitope Mapping.

A series of PA fragments differing in size were amplified from a PA-encoding vector pPA26 (Welkos S. L. et al. 1988 *Gene* 69:287-300; GenBank Accession No.: M22589) by PCR as described elsewhere (Schofield D. J. et al. 2003 *Vaccine* 22:257-67) and inserted into pGEM-T vectors (Promega, Madison, Wis.). $^{35}$S-methionine (Amersham Biosciences) labeled PA peptides were prepared with the TNT T7/SP6 coupled in vitro transcription/translation system (Promega). A radioimmunoprecipitation assay (RIPA) was performed essentially as described previously (Schofield D. J. et al. 2003 *Vaccine* 22:257-67). Briefly, a mixture of a $^{35}$S-labeled peptide and anti-PA W2 was incubated at 4° C. overnight and immune complexes were collected with protein G-coupled agarose beads (Amersham Biosciences). The precipitated complex was washed and subjected to SDS-PAGE. The PA peptide was detected by exposing the dried gel to X-ray film.

PA Binding Assays.

RAW264.7 cells (Varughese M. et al. 1998 *Mol Med* 4:87-95) were grown in 6-well plates to 90% confluence. Ten microliters of PA (10 µg/ml) was mixed with neutralizing antibody 14B7 (Little S. F. et al. 1988 *Infect Immun* 56:1807-13) or with W2 at 1:1 or 1:10 (PA:MAb) molar ratios in a 200 µl final volume and incubated for 5 min or 15 min. PBS was mixed with PA in control samples. The mixture was added to the cells and incubated for 20 min at 37° C. Medium was removed and cells were washed 5 times with ice-cold PBS followed by lysis in RIPA buffer (1% Nonidet, 0.5% sodium deoxycholate, 0.1% SDS in PBS) plus EDTA-free COMPLETE protease inhibitor cocktail (Roche Applied Science, Indianapolis, Ind.). Equal amounts of protein (BCA assay (Pierce Biotechnology)) were loaded onto SDS-PAGE gels. Western Blot analysis was performed using anti-PA polyclonal antibody 5308 (1:3500) developed in our laboratory and HRP-conjugated goat-anti-rabbit IgG secondary antibody (Santa Cruz Biotech, Santa Cruz, Calif.) at 1:2000 dilution.

In Vitro Neutralization Assay.

An established RAW264.7 cells-based assay was used to determine the antibody in vitro neutralization activity (Varughese M. et al. 1998 *Mol Med* 4:87-95; Pitt M. L. et al. 2001 *Vaccine* 19:4768-73). Results were plotted and the effective concentration for 50% neutralization ($EC_{50}$) was calculated with Prism software (Graphpad Software Inc, San Diego, Calif.).

In Vivo Neutralization Assay.

Groups of 3 Fischer 344 rats (Female, 150-170 g) were injected via the tail vein with PBS or a mixture of antibody and PA+LF (LT), at different molar ratios (1:3-4, Ab:LT), prepared in sterile PBS. Injection volumes were 200 µl/rat. Animals were observed continuously for the first 8 h, then at 16 h and 24 h, followed by twice daily checks for one week. Animals were monitored for signs of malaise and mortality. When rats were pre-treated with antibody, they were injected intravenously (IV) with PBS or antibody at 5 min, 4 h, or 1 week prior to an IV injection with PA+LF (7.5 µg each).

Results

Isolation of Anti-PA and Anti-LF Clones.

Recombinant proteins were used as antigens to select antibodies from a scFv library derived from immunized chimpanzees. After three rounds of selection with PA, LF or EF, a total of 192 phagemid clones were screened for specific binding by ELISA. We did not detect clones that bound specifically to EF protein. Ninety percent of the clones recognized PA or LF proteins but not BSA control protein. Four unique anti-PA and two unique anti-LF scFv phagemid clones were identified (W1, W2, A63-6, W5, F3-6, and F5-1) by sequence analysis (FIG. 1). Two clones, W1 and W2, had very similar sequences in VH and Vκ regions (FIG. 1) with only 9 amino acid residue differences (three of them are located within the primer region). The other four clones differed greatly in amino acid sequences. As expected, the greatest divergence in terms of sequence and length was in the CDR regions. Because there is extensive homology between chimpanzee and human Igs (Schofield D. J. et al. 2002 *Virology* 292:127-36), similarity searches of all known human Ig genes on V-BASE database (Cook G. P. et al. 1995 *Immunol Today* 16:237-42) were conducted. The VH3 family of heavy chain and the Vκ I and II families of kappa light chain were preferentially used by anti-anthrax antibodies (Table 1). As expected, W1 and W2 clones were derived from the same VH and Vκ germ line genes.

Figure 2B:
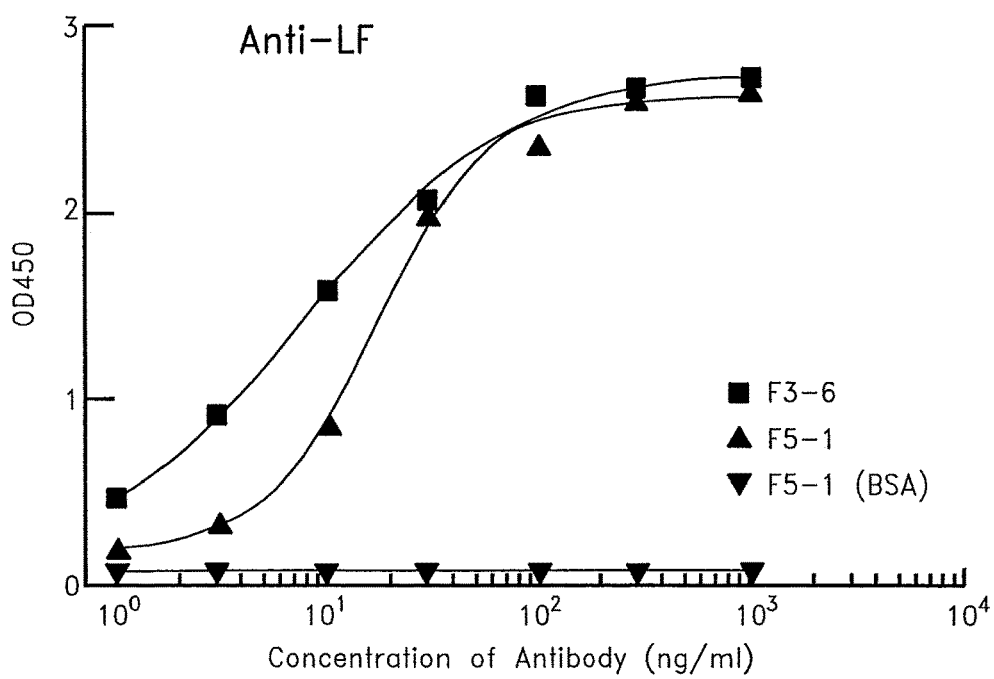

The six scFvs were expressed in *E. coli*, purified by affinity chromatography, and tested for binding activity and specificity by ELISA. Clones W1, W2, A63-6, and W5 bound strongly to PA antigen and clones F3-6 and F5-1 bound strongly to LF antigen (FIG. 2); none bound to BSA, thyroglobulin, phosphorylase-b, or lysozyme.

In Vitro Neutralizing Activity and Affinity of W1 and W2.

The effect of anthrax toxin was strongly inhibited by the W1 and W2 scFvs, but not by A63-6, F3-6, F5-1 and W5 scFvs. The latter scFvs were not further studied.

ScFv fragments have limited utilization in passive immunotherapy because these monovalent fragments are rapidly cleared from the blood. In most cases, bivalent full-length immunoglobulin is more effective than the corresponding scFv because of avidity effects, effector functions, and prolonged half-life in the blood. Therefore, W1 and W2 scFvs were converted to bivalent whole IgG1s and compared for neutralization activity in the RAW264.7 cell-based in vitro assay. Well-characterized mouse anti-PA 14B7 was used as a comparison control (Little S. F. et al. 1988 *Infect Immun* 56:1807-13).

Figure 3:
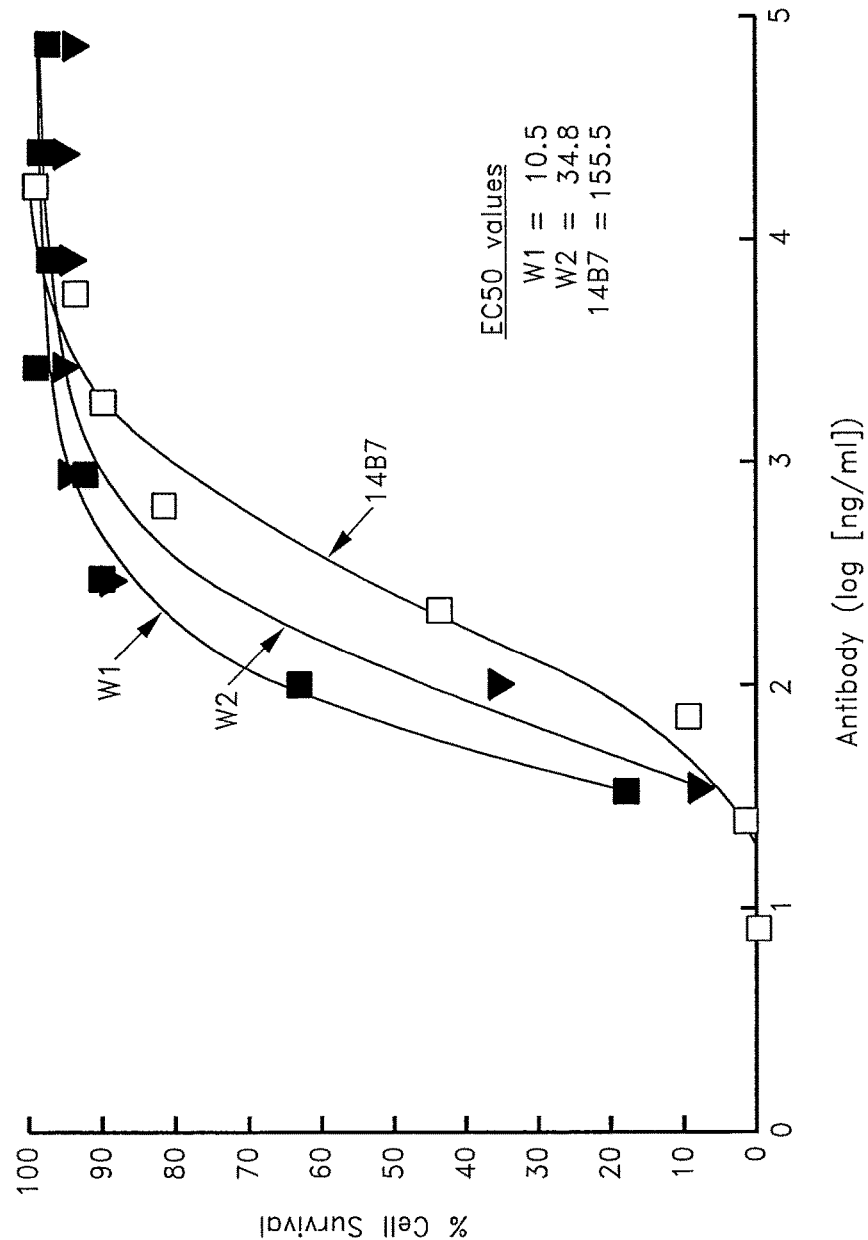
FIG. 3. In vitro neutralization assay. Anti-PA IgG was mixed with anthrax toxin and incubated at 37° C. for 1 h. The mixture was added to RAW264.7 cells in a 96-well plate and incubated at 37° C. for 4 h. After washing, the cells were stained with MTT dye followed by lysis in a solution containing 0.5% SDS in 90% isopropanol, 0.05 M HCl. The plate was read at $OD_{570}$ with $OD_{690}$ as a reference. Results were plotted and analyzed with Prism software (Graphpad Software Inc, San Diego). W1: ■; W2: ▼; 14B7: □.

Neutralization by complete IgGs was five to twenty-fold better than that by scFvs and five (W2) and fifteen (W1)-fold higher than that by mouse anti-PA 14B7 (FIG. 3). The equilibrium dissociation constant ($K_d$) for W1 and W2 IgG1 respectively was determined by Biacore analysis. W1 and W2 antibody displayed very high affinity with a IQ of $4 \times 10^{-11}$ and $5 \times 10^{-11}$ M, respectively compared to a $K_d$ of $4 \times 10^{-9}$ M for 14B7 (this study) (Table 2). These affinities compared favorably with those published for human anti-PA MAbs (Table 2) and were the highest recorded against anthrax PA (Wild M. A. et al. 2003 *Nat Biotechnol* 21:1305-6; Sawada-Hirai R. et al. 2004 *J Immune Based Ther Vaccines* 2:5; Cirino N. M. et al. 1999 *Infect Immun* 67:2957-63).

Characterization of the Neutralization Epitope and Mechanism of Neutralization.

Figure 4:
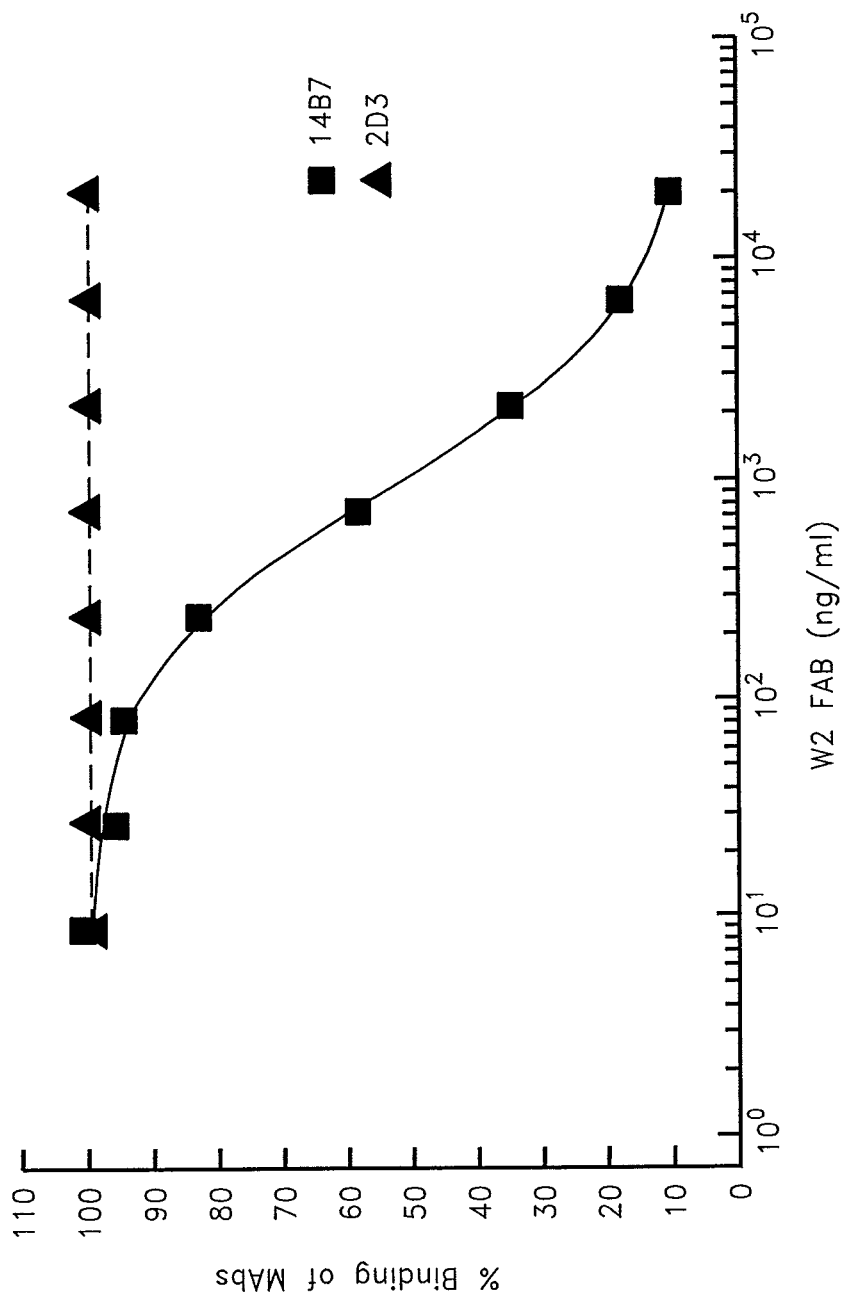
FIG. 4. Competitive ELISA. Recombinant PA was coated onto the wells of an ELISA plate. Wells were then incubated with anti-PA W2 Fab at the concentrations indicated. After incubation at room temperature for 1 h, anti-PA W2 Fab was removed from the wells and mouse anti-PA MAbs 14B7 and 2D3 (Cook, G. P. & Tomlinson, I. M. 1995 *Immunol Today* 16:237-42; Petosa, C. et al. 1997 *Nature* 385:833-8) were added to the wells. Bound MAbs were detected by the addition of peroxidase-conjugated anti-mouse antibody followed by TMB substrate. The binding to PA was calculated by dividing the OD value in the absence of W2 with that in the presence of W2.
Figure 5:
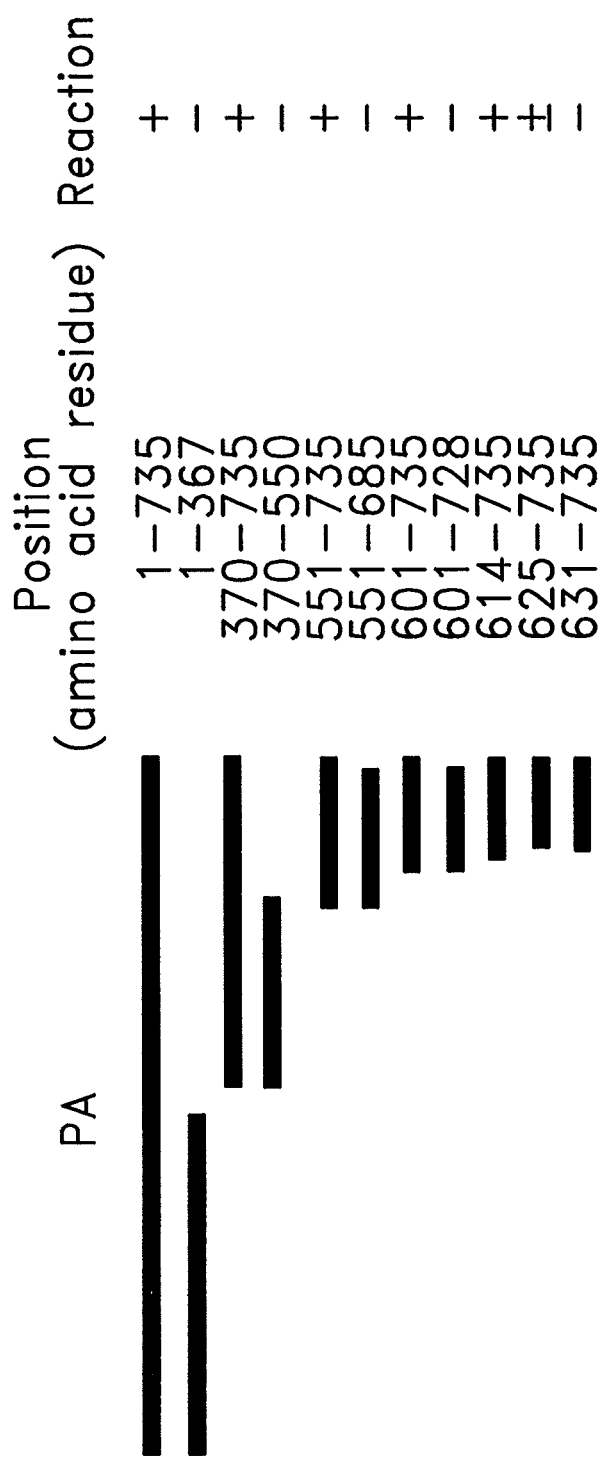
FIG. 5. Summary of epitope mapping of anti-PA W2 antibody by radioimmunoprecipitation assay (RIPA). $^{35}$S-labeled PA peptides, prepared in vitro, were incubated with anti-PA W2. The immune complexes were captured by protein G-coupled agarose beads and separated on SDS-PAGE. The PA peptide was detected by exposing the dried gel to X-ray film. The numbers denote the starting and ending amino acid. The peptides that reacted with antibody and hence were detected on X-ray film were scored as positive (+). Faint intensity of the band on X-ray film denoted partial reaction and was scored as +/−.
Figure 6:
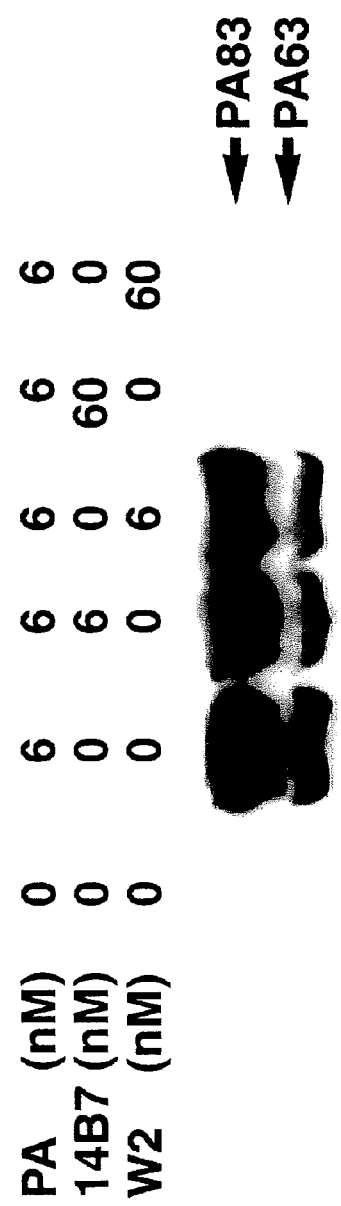
FIG. 6. Inhibition of the binding of PA to RAW264.7 cells by preincubation of toxin with mAbs. PA at concentration of 6 nM (500 ng/ml) was incubated with anti-PA 14B7 or W2 antibodies at 1:1 or 1:10 molar ratio for 5 min. The mixture was added to RAW264.7 cells and incubated for 20 min at 37° C. The cells were washed and lysed, followed by separation on SDS-PAGE. The proteins were transferred to a membrane and probed with anti-PA polyclonal antibody.
Figure 7:
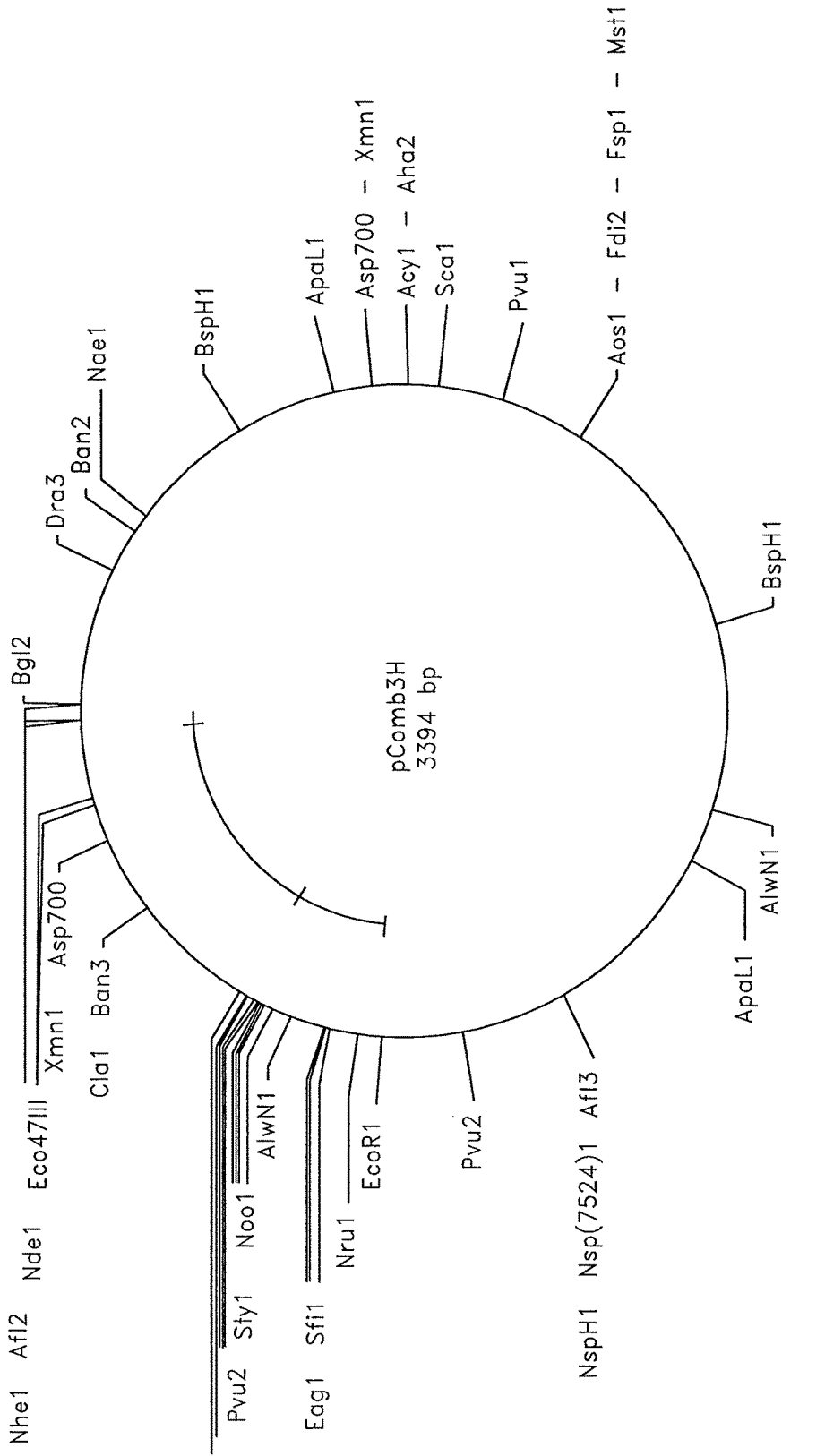
FIG. 7. pComb 3H Cut Site Map.

Competitive ELISA results indicated that W1 and W2 may recognize the same epitope since they competed with each other in binding to PA and the CDR regions of their VH chains are identical. Therefore, only W2 was used to map the neutralization epitope. Competition in ELISA was also observed between 14B7 and W2 but not between 2D3 and W2 (FIG. 4). 14B7 binds to the site responsible for binding to the cellular receptor while 2D3 does not compete 14B7 and binds to a distinct binding site (Little S. F. et al. 1996 *Microbiology* 142 (Pt 3):707-15). The binding site for W2 was mapped by radioimmunoprecipitation assay (RIPA). The smallest peptide that reacted with W2 antibody contained 121 aa, corresponding to amino acid residues 614-735 at the C-terminus of PA (FIG. 5). This result indicated that W2 bound to a conformational epitope that encompassed almost the entire domain 4 of PA (Petosa C. et al. 1997 *Nature* 385:833-8). Since domain 4 of PA is responsible for cellular receptor binding (Varughese M. et al. 1999 *Infect Immun* 67:1860-5; Liu S. et al. 2003 *J Biol Chem* 278:5227-34), the results indicated that W2 neutralizes the toxin by blocking binding of PA to the cellular receptor. This conclusion was confirmed in a binding assay by Western blot, which showed that W2 prevented the binding of PA to RAW264.7 cells (FIG. 6). The affinity ($K_d$) of binding of PA to the receptor is $1-5\times10^{-9}$ M (Singh Y. et al. 1989 *J Biol Chem* 264:19103-7). Therefore, the affinity of W2 antibody binding to PA is 20-100-fold higher than the affinity of PA for the cellular receptor.

In Vivo Animal Protection.

Since affinity of anti-PA is strongly correlated with its neutralization activity, it is reasonable to assume that anti-PA W1 and W2 are potent neutralizing antibodies. As has been reported for other anti-PA MAbs (Wild M. A. et al. 2003 *Nat Biotechnol* 21:1305-6; Sawada-Hirai R. et al. 2004 *J Immune Based Ther Vaccines* 2:5), one remarkable feature of our antibodies is the very slow off-rate, which is envisioned as providing a significant physiological advantage for toxin neutralization in vivo.

To evaluate the neutralization of PA by W1 and W2 in vivo, we measured protection against toxin challenge in the Fisher 344 rat model in two ways. First, MAb and toxin were mixed at different molar ratios and the mixtures were injected into 3 rats each which were observed for morbidity and mortality. Injection of 7.5 µg of LT (7.5 µg PA+7.5 µg LF) toxin alone killed all three rats within 100-134 min (Table 3). W2 antibody conferred protection at very low concentrations. Addition of W2 antibody at a molar ratio of 1:4 (Ab:PA), the lowest concentration of antibody tested, completely protected the rats from toxin challenge. In comparison, 14B7 mouse antibody protected only one of the three rats at this ratio, probably reflecting the difference in affinity between W2 and 14B7.

Second, as a more stringent test, the MAb was injected 5 min, 4 h, and 1 week before injection of LT (7.5 µg PA+7.5 µg LF) to investigate the duration of antibody protection. Single administration of W1 and W2 antibodies at a 2:1 molar ratio of Ab to PA protected 6 of 6 rats challenged with toxin 5 min, 4 h or 1 week later (Table 4). A lower dose of antibodies (0.5:1) still protected all the rats (n=6) when they were challenged 5 min or 4 h later, but not when they were challenged one week later (Table 4).

Discussion

We have identified two chimpanzee monoclonal antibodies, W1 and W2, which bind to PA with high affinity. These antibodies neutralized cytotoxicity of anthrax toxin in the picomolar range in vitro and efficiently protected animals from toxin challenge in vivo, most likely by blocking binding to the cell receptor. Our two neutralizing MAbs have the highest affinity of any human antibodies for PA reported thus far. Antibody affinity has been shown to correlate well with efficacy (Maynard J. A. et al. 2002 *Nat Biotechnol* 20:597-601; Adams G. P. et al. 1998 *Cancer Res* 58:485-90; Bachmann M. F. et al. 1997 *Science* 276:2024-7; Jackson H. et al. 1998 *Br J Cancer* 78:181-8; Lamarre A. et al. 1991 *J Immunol* 147:4256-62; Lamarre A. & Talbot P. J. 1995 *J Immunol* 154:3975-84).

The neutralization epitope recognized by W1 and W2 MAbs was mapped to a region of PA comprising residues 614 to 735. So far, three neutralization epitopes in PA have been proposed; the site for binding to the cellular receptor, the site for binding to LF (Little S. F. et al. 1996 *Microbiology* 142 (Pt 3):707-15; Brossier F. et al. 2004 *Infect Immun* 72:6313-7), and the site for heptamer formation (Brossier F. et al. 2004 *Infect Immun* 72:6313-7). However, the locations of these putative epitopes have not been precisely defined. For example, the epitope recognized by murine MAb 14B7 was suggested to be between Asp-671 and Ile-721 based on the differential binding of 14B7 to different PA fragments generated through C-terminal deletions (Little S. F. et al. 1996 *Microbiology* 142 (Pt 3):707-15). Since N-terminally deleted PA fragments were not tested, the epitope mapping for 14B7 could be incomplete. The previous observation that a PA fragment corresponding to residues 624-735 did not compete with PA for binding to the cell receptor (Singh Y. et al. 1991 *J Biol Chem* 266:15493-7) indicates that the region between residues 624-735 was not sufficient to generate the receptor recognition site. Some of the residues in domain 4 of PA that are critical for binding to the cellular receptor and to anti-PA 14B7 MAb have been determined by alanine-scanning mutations (Rosovitz M. J. et al. 2003 *J Biol Chem* 278:30936-44).

Anthrax, whether resulting from natural or bioterrorist-associated exposure, represents a constant threat to human health. Although production of an efficient vaccine is an ultimate goal, the benefits of vaccination can be expected only if a large proportion of the population at risk is immunized. The low incidence of anthrax suggests that large-scale vaccination may not be the most efficient means of controlling this disease. In contrast, passive administration of neutralizing human or chimpanzee monoclonal antibody to an at-risk or exposed subject could provide immediate efficacy for emergency prophylaxis or therapy of anthrax. This is supported by a recent publication (Mohamed N. et al. 2005 *Infect Immun* 73:795-802), which indicated that passive immunization with affinity-improved, humanized murine MAb 14B7 against PA, ETI-204, could efficiently protect rabbits before or after challenge with aerosolized *Bacillus anthracis* spores. However, humanized murine MAbs may retain some antigenic components of the original murine sequences and elicit antibodies to the MAb in humans. Human and chimpanzee derived MAbs would not be expected to have this problem because the sequences of chimpanzee immunoglobulin genes are virtually identical to those of humans (Schofield D. J. et al. 2002 *Virology* 292:127-36; Ehrlich P. H. et al. 1988 *Clin Chem* 34:1681-8; Ehrlich P. H. et al. 1990 *Hum Antibodies Hybridomas* 1:23-6; Schofield D. J. et al. 2000 *J Virol* 74:5548-55). Furthermore, one would expect that the anti-PA chimpanzee MAbs, W1 and W2 will provide better protection than ETI-204, since these MAbs had higher affinity ($K_d$) and lower $EC_{50}$ in in vitro neutralization experiments than did ETI-204.

TABLE 1

Human Ig Germ Line Genes Most Closely Related to Chimpanzee Heavy and Kappa Light Chains of Various Anti-anthrax PA and LF Antibodies.

| MAb | VH Family | VH Segment | D Segment | JH Segment | Vκ Family | Vκ Segment | Jκ Segment |
|---|---|---|---|---|---|---|---|
| W1 | VH3 | DP-42 | ND | J6c | Vκ II | DPK-15 | Jκ3 |
| W2 | VH3 | DP-42 | ND | J6c | Vκ II | DPK-15 | Jκ1 |
| W5 | VH4 | DP-78 | D2-15 | J5b | Vκ II | A2b | Jκ4 |
| A63-6 | VH3 | DP-47 | D1-14 | J6c | Vκ I | HK 102 | Jκ4 |
| F3-6 | VH3 | DP-49 | ND | J4b | Vκ I | HK 102 | Jκ5 |
| F5-1 | VH5 | DP-73 | ND | J6c | Vκ I | HK 102 | Jκ1 |

The closest human VH and Vκ germ line genes were identified by V-BASE database (Cook G. P. et al. 1995 *Immunol Today* 16: 237-42).
ND, not determined due to lack of identifiable homologue.

TABLE 2

Affinity of Anti-anthrax PA W1 and W2 Antibodies Compared with Other Human Anti-PA MAbs

| Antibody | Association Rate $k_{on}$ (M$^{-1}$s$^{-1}$) | Dissociation Rate $k_{off}$ (s$^{-1}$) | Dissociation Constant $K_d$ (M) | Reference |
|---|---|---|---|---|
| W1 | $2.90 \times 10^5$ | $1.15 \times 10^{-5}$ | $3.97 \times 10^{-11}$ | this study |
| W2 | $2.77 \times 10^5$ | $1.52 \times 10^{-5}$ | $5.49 \times 10^{-11}$ | this study |
| AVP-21D9 | $1.8 \times 10^5$ | $1.48 \times 10^{-5}$ | $8.21 \times 10^{-11}$ | Sawada-Hirai R. et al. 2004 J Immune Based Ther Vaccines 2:5 |
| AVP-1C6 | $1.85 \times 10^5$ | $1.31 \times 10^{-4}$ | $7.11 \times 10^{-10}$ | Sawada-Hirai R. et al. 2004 J Immune Based Ther Vaccines 2:5 |
| AVP-4H7 | $1.74 \times 10^5$ | $2.45 \times 10^{-5}$ | $1.41 \times 10^{-10}$ | Sawada-Hirai R. et al. 2004 J Immune Based Ther Vaccines 2:5 |
| AVP-22G12 | $1.01 \times 10^5$ | $5.17 \times 10^{-5}$ | $5.12 \times 10^{-10}$ | Sawada-Hirai R. et al. 2004 J Immune Based Ther Vaccines 2:5 |
| 83K7C | $1.16 \times 10^5$ | $4.26 \times 10^{-4}$ | $3.67 \times 10^{-9}$ | Wild M.A. et al. 2003 Nat Biotechnol 21:1305-6 |
| 63L1D | $1.50 \times 10^6$ | $1.90 \times 10^{-4}$ | $1.3 \times 10^{-10}$ | Wild M.A. et al. 2003 Nat Biotechnol 21:1305-6 |
| scFv1 | NA | NA | $1.9 \times 10^{-7}$ | Cook G.P. et al. 1995 Immunol Today 16:237-42 |
| scFv4 | NA | NA | $3.1 \times 10^{-7}$ | Cook G.P. et al. 1995 Immunol Today 16:237-42 |
| scFv12 | NA | NA | $1.1 \times 10^{-6}$ | Cook G.P. et al. 1995 Immunol Today 16:237-42 |
| scFv24 | NA | NA | $4.3 \times 10^{-7}$ | Cook G.P. et al. 1995 Immunol Today 16:237-42 |
| ETI-204[a] | $4.57 \times 10^5$ | $1.50 \times 10^{-4}$ | $3.3 \times 10^{-10}$ | Mohamed N. et al. 2005 Infect Immun 73:795-802 |

[a]ETI-204 is an affinity-improved, humanized MAb derived from murine MAb 14B7.

TABLE 3

Rat Protection Assay [a]

| Antibody | Molar ratios of MAb to PA[b] | Rat surviving/ rat injected |
|---|---|---|
| — | LT only (7.5 μg) | 0/5[c] |
| 14B7 | 1:4 | 1/3[d] |
| W2 | 1:4 | 3/3 |
| 14B7 | 1:3 | 3/3 |
| W2 | 1:3 | 3/3 |

[a] Antibody and LT (PA + LF) was mixed at indicated molar ratios and injected IV
[b] The amount of PA was kept constant as 7.5 μg.
[c] Time to death was 100-134 min
[d] Time to death was 128 and 168 min

TABLE 4

| | Rat Protection Assay | | | | | | | | |
|---|---|---|---|---|---|---|---|---|---|
| MAb: | Interval between injection of rats with MAb and injection with PA plus LF[a] | | | | | | | | |
| Molar ratio | 5 min | | | 4 h | | | 1 week | | |
| of MAb to PA | W1 | W2 | Combined | W1 | W2 | Combined | W1 | W2 | Combined |
| 2:1 | 3/3[b] | 3/3 | 6/6 | 3/3 | 3/3 | 6/6 | 3/3 | 3/3 | 6/6 |
| 0.5:1 | 3/3 | 3/3 | 6/6 | 3/3 | 3/3 | 6/6 | 0/3 | 0/2 | 0/5 |
| 0:1 | 0/3 | 0/3 | 0/6 | 0/3 | 0/3 | 0/6 | 0/3 | 0/3 | 0/6 |

[a]7.5 µg of Protective Antigen plus 7.5 µg of Lethal Factor.
Animals surviving/animals injected While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. An isolated nucleic acid comprising a nucleotide sequence encoding a polypeptide that binds anthrax protective antigen (PA), wherein said polypeptide is selected from the group consisting of:
   a polypeptide comprising amino acid sequences SEQ ID NO: 1 and SEQ ID NO: 9; and
   a polypeptide comprising amino acid sequences SEQ ID NO:17 and SEQ ID NO: 25.

2. A vector comprising the isolated nucleic acid of claim 1 operably linked to a regulatory sequence.

3. The vector of claim 2, wherein the vector is pComb3H vector deposited with ATCC as ATCC Accession No. PTA-6293, and wherein the pComb3H vector contains the nucleotide sequence encoding the polypeptide consisting of amino acid sequences SEQ ID NO:1 and SEQ ID NO:9.

4. A host cell including a vector comprising a nucleic acid of claim 1.

5. The vector of claim 2, wherein the vector is pComb3H vector deposited with ATCC as ATCC Accession No. PTA-6409, and wherein the pComb3H vector contains the nucleotide sequence encoding the polypeptide consisting of amino acid sequences SEQ ID NO:17 and SEQ ID NO:25.

6. The isolated nucleic acid of claim 1, wherein said polypeptide comprises amino acid sequences SEQ ID NO:1 and SEQ ID NO:9.

7. A preparation comprising the isolated nucleic acid of claim 6 and a pharmaceutically acceptable carrier.

8. The isolated nucleic acid of claim 1, wherein said polypeptide comprises amino acid sequences SEQ ID NO:17 and SEQ ID NO:25.

9. A preparation comprising the isolated nucleic acid of claim 8 and a pharmaceutically acceptable carrier.

* * * * *

SEQUENCE LISTING

```
<160> NUMBER OF SEQ ID NOS: 48

<210> SEQ ID NO 1
<211> LENGTH: 121
<212> TYPE: PRT
<213> ORGANISM: Artificial Sequence
<220> FEATURE:
<223> OTHER INFORMATION: Monoclonal antibody

<400> SEQUENCE: 1

Glu Val Gln Leu Leu Glu Thr Gly Gly Gly Leu Val Gln Pro Gly Gly
 1               5                  10                  15

Ser Leu Arg Leu Ser Cys Ala Ala Ser Gly Phe Thr Leu Arg Ser Tyr
             20                  25                  30

His Met Ser Trp Val Arg Arg Ala Pro Gly Lys Gly Leu Glu Trp Val
         35                  40                  45

Ser Val Ile Tyr Asp Gly Gly Ser Thr Ser Tyr Ala Asp Ser Val Lys
     50                  55                  60

Gly Arg Phe Thr Ile Ser Arg Asp Asn Ser Lys Asn Thr Leu Tyr Leu
 65                  70                  75                  80

Gln Met Thr Ser Leu Arg Ala Glu Asp Thr Ala Val Tyr Tyr Cys Ala
                 85                  90                  95

Arg Ser Gly Arg Pro Leu Gln Asn Tyr Tyr Tyr Met Asp Val Trp Gly
            100                 105                 110

Lys Gly Thr Thr Val Thr Val Ser Ser
        115                 120

<210> SEQ ID NO 2
<211> LENGTH: 30
<212> TYPE: PRT
<213> ORGANISM: Artificial Sequence
<220> FEATURE:
<223> OTHER INFORMATION: Monoclonal antibody

<400> SEQUENCE: 2

Glu Val Gln Leu Leu Glu Thr Gly Gly Gly Leu Val Gln Pro Gly Gly
 1               5                  10                  15

Ser Leu Arg Leu Ser Cys Ala Ala Ser Gly Phe Thr Leu Arg
             20                  25                  30

<210> SEQ ID NO 3
<211> LENGTH: 5
```

```
<212> TYPE: PRT
<213> ORGANISM: Artificial Sequence
<220> FEATURE:
<223> OTHER INFORMATION: Monoclonal antibody

<400> SEQUENCE: 3

Ser Tyr His Met Ser
1               5

<210> SEQ ID NO 4
<211> LENGTH: 14
<212> TYPE: PRT
<213> ORGANISM: Artificial Sequence
<220> FEATURE:
<223> OTHER INFORMATION: Monoclonal antibody

<400> SEQUENCE: 4

Trp Val Arg Arg Ala Pro Gly Lys Gly Leu Glu Trp Val Ser
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Monoclonal antibody

<400> SEQUENCE: 5

Val Ile Tyr Asp Gly Gly Ser Thr Ser Tyr Ala Asp Ser Val Lys Gly
1               5                   10                  15

<210> SEQ ID NO 6
<211> LENGTH: 32
<212> TYPE: PRT
<213> ORGANISM: Artificial Sequence
<220> FEATURE:
<223> OTHER INFORMATION: Monoclonal antibody

<400> SEQUENCE: 6

Arg Phe Thr Ile Ser Arg Asp Asn Ser Lys Asn Thr Leu Tyr Leu Gln
1               5                   10                  15

Met Thr Ser Leu Arg Ala Glu Asp Thr Ala Val Tyr Tyr Cys Ala Arg
            20                  25                  30

<210> SEQ ID NO 7
<211> LENGTH: 13
<212> TYPE: PRT
<213> ORGANISM: Artificial Sequence
<220> FEATURE:
<223> OTHER INFORMATION: Monoclonal antibody

<400> SEQUENCE: 7

Ser Gly Arg Pro Leu Gln Asn Tyr Tyr Tyr Met Asp Val
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Monoclonal antibody

<400> SEQUENCE: 8

Trp Gly Lys Gly Thr Thr Val Thr Val Ser Ser
1               5                   10
```

<210> SEQ ID NO 9
<211> LENGTH: 113
<212> TYPE: PRT
<213> ORGANISM: Artificial Sequence
<220> FEATURE:
<223> OTHER INFORMATION: Monoclonal antibody

<400> SEQUENCE: 9

Glu Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Arg Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Phe Thr Phe Gly Pro Gly Thr Lys Val Glu Ile Lys
            100                 105                 110

Arg

<210> SEQ ID NO 10
<211> LENGTH: 23
<212> TYPE: PRT
<213> ORGANISM: Artificial Sequence
<220> FEATURE:
<223> OTHER INFORMATION: Monoclonal antibody

<400> SEQUENCE: 10

Glu Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 11
<211> LENGTH: 16
<212> TYPE: PRT
<213> ORGANISM: Artificial Sequence
<220> FEATURE:
<223> OTHER INFORMATION: Monoclonal antibody

<400> SEQUENCE: 11

Arg Ser Ser Gln Ser Leu Leu His Ser Asn Arg Tyr Asn Tyr Leu Asp
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Monoclonal antibody

<400> SEQUENCE: 12

Trp Tyr Leu Gln Lys Pro Gly Gln Ser Pro Gln Leu Leu Ile Tyr
1               5                   10                  15

<210> SEQ ID NO 13
<211> LENGTH: 7
<212> TYPE: PRT
<213> ORGANISM: Artificial Sequence
<220> FEATURE:
<223> OTHER INFORMATION: Monoclonal antibody

<400> SEQUENCE: 13

Leu Gly Ser Asn Arg Ala Ser
1               5

<210> SEQ ID NO 14
<211> LENGTH: 32
<212> TYPE: PRT
<213> ORGANISM: Artificial Sequence
<220> FEATURE:
<223> OTHER INFORMATION: Monoclonal antibody

<400> SEQUENCE: 14

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 15
<211> LENGTH: 9
<212> TYPE: PRT
<213> ORGANISM: Artificial Sequence
<220> FEATURE:
<223> OTHER INFORMATION: Monoclonal antibody

<400> SEQUENCE: 15

Met Gln Ala Leu Gln Thr Pro Phe Thr
1               5

<210> SEQ ID NO 16
<211> LENGTH: 11
<212> TYPE: PRT
<213> ORGANISM: Artificial Sequence
<220> FEATURE:
<223> OTHER INFORMATION: Monoclonal antibody

<400> SEQUENCE: 16

Phe Gly Pro Gly Thr Lys Val Glu Ile Lys Arg
1               5                   10

<210> SEQ ID NO 17
<211> LENGTH: 121
<212> TYPE: PRT
<213> ORGANISM: Artificial Sequence
<220> FEATURE:
<223> OTHER INFORMATION: Monoclonal antibody

<400> SEQUENCE: 17

Glu Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Leu Arg Ser Tyr
            20                  25                  30

His Met Ser Trp Val Arg Lys Ala Pro Gly Lys Gly Leu Glu Trp Val
        35                  40                  45

Ser Val Ile Tyr Asp Gly Gly Ser Thr Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Thr Ser Leu Arg Ala Glu Asp Thr Ala Val Tyr Tyr Cys Ala
                85                  90                  95

Arg Ser Gly Arg Pro Leu Gln Asn Tyr Tyr Tyr Met Asp Val Trp Gly

```
                100               105                110
Lys Gly Thr Thr Val Thr Val Ser Ser
        115                 120

<210> SEQ ID NO 18
<211> LENGTH: 30
<212> TYPE: PRT
<213> ORGANISM: Artificial Sequence
<220> FEATURE:
<223> OTHER INFORMATION: Monoclonal antibody

<400> SEQUENCE: 18

Glu Val Gln Leu Val Glu Thr Gly Gly Leu Val Gln Pro Gly Gly
1               5                   10                  15

Ser Leu Arg Leu Ser Cys Ala Ala Ser Gly Phe Thr Leu Arg
            20                  25                  30

<210> SEQ ID NO 19
<211> LENGTH: 5
<212> TYPE: PRT
<213> ORGANISM: Artificial Sequence
<220> FEATURE:
<223> OTHER INFORMATION: Monoclonal antibody

<400> SEQUENCE: 19

Ser Tyr His Met Ser
1               5

<210> SEQ ID NO 20
<211> LENGTH: 14
<212> TYPE: PRT
<213> ORGANISM: Artificial Sequence
<220> FEATURE:
<223> OTHER INFORMATION: Monoclonal antibody

<400> SEQUENCE: 20

Trp Val Arg Lys Ala Pro Gly Lys Gly Leu Glu Trp Val Ser
1               5                   10

<210> SEQ ID NO 21
<211> LENGTH: 16
<212> TYPE: PRT
<213> ORGANISM: Artificial Sequence
<220> FEATURE:
<223> OTHER INFORMATION: Monoclonal antibody

<400> SEQUENCE: 21

Val Ile Tyr Asp Gly Gly Ser Thr Ser Tyr Ala Asp Ser Val Lys Gly
1               5                   10                  15

<210> SEQ ID NO 22
<211> LENGTH: 32
<212> TYPE: PRT
<213> ORGANISM: Artificial Sequence
<220> FEATURE:
<223> OTHER INFORMATION: Monoclonal antibody

<400> SEQUENCE: 22

Arg Phe Thr Ile Ser Arg Asp Asn Ser Lys Asn Thr Leu Tyr Leu Gln
1               5                   10                  15

Met Thr Ser Leu Arg Ala Glu Asp Thr Ala Val Tyr Tyr Cys Ala Arg
            20                  25                  30

<210> SEQ ID NO 23
<211> LENGTH: 13
```

```
<212> TYPE: PRT
<213> ORGANISM: Artificial Sequence
<220> FEATURE:
<223> OTHER INFORMATION: Monoclonal antibody

<400> SEQUENCE: 23

Ser Gly Arg Pro Leu Gln Asn Tyr Tyr Tyr Met Asp Val
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Monoclonal antibody

<400> SEQUENCE: 24

Trp Gly Lys Gly Thr Thr Val Thr Val Ser Ser
1               5                   10

<210> SEQ ID NO 25
<211> LENGTH: 113
<212> TYPE: PRT
<213> ORGANISM: Artificial Sequence
<220> FEATURE:
<223> OTHER INFORMATION: Monoclonal antibody

<400> SEQUENCE: 25

Glu Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Thr Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Gly Arg Phe Ser Gly Ser Gly Ser Gly Thr Asp Phe Thr Leu Lys Ile
65                  70                  75                  80

Ser Arg Val Glu Ala Glu Asp Ile Gly Val Tyr Tyr Cys Met Gln Ala
                85                  90                  95

Leu Gln Thr Pro Leu Thr Phe Gly Gln Gly Thr Lys Val Lys Ile Lys
            100                 105                 110

Ala

<210> SEQ ID NO 26
<211> LENGTH: 23
<212> TYPE: PRT
<213> ORGANISM: Artificial Sequence
<220> FEATURE:
<223> OTHER INFORMATION: Monoclonal antibody

<400> SEQUENCE: 26

Glu Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 27
<211> LENGTH: 16
<212> TYPE: PRT
<213> ORGANISM: Artificial Sequence
<220> FEATURE:
<223> OTHER INFORMATION: Monoclonal antibody
```

<400> SEQUENCE: 27

Arg Ser Ser Gln Ser Leu Leu His Ser Asn Thr Tyr Asn Tyr Leu Asp
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Monoclonal antibody

<400> SEQUENCE: 28

Trp Tyr Leu Gln Lys Pro Gly Gln Ser Pro Gln Leu Leu Ile Tyr
1               5                   10                  15

<210> SEQ ID NO 29
<211> LENGTH: 7
<212> TYPE: PRT
<213> ORGANISM: Artificial Sequence
<220> FEATURE:
<223> OTHER INFORMATION: Monoclonal antibody

<400> SEQUENCE: 29

Leu Gly Ser Asn Arg Ala Ser
1               5

<210> SEQ ID NO 30
<211> LENGTH: 32
<212> TYPE: PRT
<213> ORGANISM: Artificial Sequence
<220> FEATURE:
<223> OTHER INFORMATION: Monoclonal antibody

<400> SEQUENCE: 30

Gly Val Pro Gly Arg Phe Ser Gly Ser Gly Ser Gly Thr Asp Phe Thr
1               5                   10                  15

Leu Lys Ile Ser Arg Val Glu Ala Glu Asp Ile Gly Val Tyr Tyr Cys
                20                  25                  30

<210> SEQ ID NO 31
<211> LENGTH: 9
<212> TYPE: PRT
<213> ORGANISM: Artificial Sequence
<220> FEATURE:
<223> OTHER INFORMATION: Monoclonal antibody

<400> SEQUENCE: 31

Met Gln Ala Leu Gln Thr Pro Leu Thr
1               5

<210> SEQ ID NO 32
<211> LENGTH: 11
<212> TYPE: PRT
<213> ORGANISM: Artificial Sequence
<220> FEATURE:
<223> OTHER INFORMATION: Monoclonal antibody

<400> SEQUENCE: 32

Phe Gly Gln Gly Thr Lys Val Lys Ile Lys Ala
1               5                   10

<210> SEQ ID NO 33
<211> LENGTH: 125
<212> TYPE: PRT
<213> ORGANISM: Artificial Sequence
<220> FEATURE:
<223> OTHER INFORMATION: Monoclonal antibody

<400> SEQUENCE: 33

Gln Val Gln Leu Gln Glu Ser Gly Pro Gly Leu Val Lys Pro Ser Gln
1               5                   10                  15

Thr Leu Ser Leu Thr Cys Ala Val Ser Ala Asp Ser Ile Thr Ser Gly
            20                  25                  30

Tyr Tyr Tyr Trp Asn Trp Ile Arg Gln Pro Pro Gly Lys Gly Leu Glu
        35                  40                  45

Trp Ile Ala Tyr Ile Asp Tyr Arg Gly Thr Thr Thr Tyr Asn Pro Ser
    50                  55                  60

Leu Lys Ser Arg Val Thr Met Ser Leu Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Gly Gly Tyr Pro Gln Tyr Gly Asp Tyr Ala Trp Phe
            100                 105                 110

Asp Pro Trp Gly Gln Gly Thr Thr Val Thr Val Ser Ser
        115                 120                 125

<210> SEQ ID NO 34
<211> LENGTH: 125
<212> TYPE: PRT
<213> ORGANISM: Artificial Sequence
<220> FEATURE:
<223> OTHER INFORMATION: Monoclonal antibody

<400> SEQUENCE: 34

Glu Val Gln Leu Val Glu Thr Gly Gly Gly Phe Val Lys Pro Gly Gly
1               5                   10                  15

Ser Leu Arg Val Ser Cys Ala Ala Ser Gly Phe Thr Phe Ser Asp Tyr
            20                  25                  30

Ala Met His Trp Val Arg Gln Ala Pro Glu Lys Gly Leu Glu Trp Val
        35                  40                  45

Ser Thr Ile Ser Gly Ser Gly Thr Ser Trp Thr Tyr Asn Pro Ser Leu
    50                  55                  60

Lys Ser Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Pro Met Val Gly Val Pro Gln Phe Tyr Tyr Tyr Tyr Ile
            100                 105                 110

Asp Pro Trp Gly Lys Gly Thr Thr Val Thr Val Ser Ser
        115                 120                 125

<210> SEQ ID NO 35
<211> LENGTH: 124
<212> TYPE: PRT
<213> ORGANISM: Artificial Sequence
<220> FEATURE:
<223> OTHER INFORMATION: Monoclonal antibody

<400> SEQUENCE: 35

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
          35                  40                  45

Ala Phe Ile Ala Phe Asp Glu Gly Asn Gln His Tyr Asn Pro Ser Leu
 50                  55                  60

Arg Ser Arg Phe Thr Ile Ser Arg Asp Asn Ser Lys Asn Thr Leu Tyr
 65                  70                  75                  80

Leu Gln Met Asn Arg Leu Arg Thr Glu Asp Thr Ala Val Tyr Tyr Cys
                 85                  90                  95

Val Arg Gly Arg Ala Ala Gly His Pro Gly Ala Ser Tyr Tyr Phe Asp
                100                 105                 110

Tyr Trp Gly Gln Gly Thr Pro Val Thr Val Ser Ser
            115                 120

<210> SEQ ID NO 36
<211> LENGTH: 129
<212> TYPE: PRT
<213> ORGANISM: Artificial Sequence
<220> FEATURE:
<223> OTHER INFORMATION: Monoclonal antibody

<400> SEQUENCE: 36

Glu Val Gln Leu Val Glu Ser Gly Ala Glu Val Lys Lys Pro Gly Glu
 1               5                  10                  15

Ser Leu Lys Ile Ser Cys Lys Ala Ser Gly Tyr Ser Phe Thr Asn Tyr
                 20                  25                  30

Trp Ile Gly Trp Val Arg Gln Met Pro Gly Lys Gly Leu Glu Trp Met
             35                  40                  45

Gly Ser Ile Tyr Pro Gly Asp Ser Asp Thr Arg Tyr Ser Pro Ser Phe
 50                  55                  60

Gln Ser Gln Val Thr Ile Ser Ala Asp Lys Ser Ile Asn Thr Ala Tyr
 65                  70                  75                  80

Leu Gln Trp Ser Ser Leu Lys Ala Ser Asp Thr Ala Ile Tyr Tyr Cys
                 85                  90                  95

Ala Arg Val Gly Ile Tyr Cys Ser Gly Asn Thr Cys Leu Ala Pro Ser
                100                 105                 110

Gly Tyr Tyr Met Asp Val Trp Gly Asn Gly Thr Thr Val Thr Val Ser
            115                 120                 125

Ser

<210> SEQ ID NO 37
<211> LENGTH: 113
<212> TYPE: PRT
<213> ORGANISM: Artificial Sequence
<220> FEATURE:
<223> OTHER INFORMATION: Monoclonal antibody

<400> SEQUENCE: 37

Asp Ile Val Met Thr Gln Ser Pro Leu Ser Leu Ser Val Thr Pro Gly
 1               5                  10                  15

Gln Pro Ala Ser Ile Ser Cys Lys Ser Ser Gln Ser Leu Leu His Ser
                 20                  25                  30

Asp Gly Asn Thr Tyr Leu Tyr Trp Tyr Leu Gln Lys Pro Gly Gln Ser
             35                  40                  45

Pro Gln Leu Leu Ile Tyr Arg Val Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

```
Ser Gln Val Glu Ala Glu Asp Val Gly Val Tyr Tyr Cys Met Gln Gly
            85                  90                  95

Ile Gln Leu Pro Leu Thr Phe Gly Gly Gly Thr Lys Val Glu Ile Lys
            100                 105                 110

Ala

<210> SEQ ID NO 38
<211> LENGTH: 108
<212> TYPE: PRT
<213> ORGANISM: Artificial Sequence
<220> FEATURE:
<223> OTHER INFORMATION: Monoclonal antibody

<400> SEQUENCE: 38

Asp Ile Leu Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Tyr Ala Ser Lys Leu Glu Ser Gly Val Pro Ser Arg Phe Ser Gly
    50                  55                  60

Ser Gly Ser Gly Pro Asp Tyr Thr Leu Thr Ile Ser Ser Leu Gln Pro
65                  70                  75                  80

Glu Asp Ser Ala Thr Tyr Phe Cys Gln Gln Tyr Ser Thr Asn Pro Leu
                85                  90                  95

Ser Phe Gly Gly Gly Thr Lys Leu Glu Ile Lys Ala
            100                 105

<210> SEQ ID NO 39
<211> LENGTH: 108
<212> TYPE: PRT
<213> ORGANISM: Artificial Sequence
<220> FEATURE:
<223> OTHER INFORMATION: Monoclonal antibody

<400> SEQUENCE: 39

Asp Ile Arg Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Thr Trp
            20                  25                  30

Leu Ala Trp Tyr Gln Gln Lys Pro Gly Arg Ala Pro Lys Pro Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys Arg
            100                 105

<210> SEQ ID NO 40
<211> LENGTH: 108
<212> TYPE: PRT
<213> ORGANISM: Artificial Sequence
<220> FEATURE:
<223> OTHER INFORMATION: Monoclonal antibody

<400> SEQUENCE: 40
```

```
Asp Ile Val Leu Thr Gln Ser Pro Ser Ser Leu Ser Ala Ser Leu Gly
 1               5                  10                  15

Asp Arg Val Thr Ile Thr Cys Trp Ala Ser Gln Gly Ile Thr Thr Arg
                20                  25                  30

Leu Asn Trp Tyr Gln His Lys Pro Gly Lys Pro Pro Lys Leu Leu Ile
             35                  40                  45

Tyr Asp Ala Ser Arg Leu Gly Ser Gly Val Pro Ser His Phe Ser Gly
 50                  55                  60

Ser Gly Ser Gly Thr Asp Phe Thr Leu Thr Ile Asn Ser Leu Gln Pro
65                  70                  75                  80

Glu Asp Phe Ala Thr Tyr Phe Cys Gln Gln Phe Lys Met Tyr Pro Pro
                 85                  90                  95

Thr Phe Gly Gln Gly Thr Lys Val Asp Ile Lys Ala
            100                 105
```

<210> SEQ ID NO 41
<211> LENGTH: 35
<212> TYPE: DNA
<213> ORGANISM: Artificial Sequence
<220> FEATURE:
<223> OTHER INFORMATION: synthetic primer

<400> SEQUENCE: 41
accgtctcct cagcctccac caagggccca tcggt           35

<210> SEQ ID NO 42
<211> LENGTH: 32
<212> TYPE: DNA
<213> ORGANISM: Artificial Sequence
<220> FEATURE:
<223> OTHER INFORMATION: synthetic primer

<400> SEQUENCE: 42
aatgagatct gcggccgctt aaattaatta at              32

<210> SEQ ID NO 43
<211> LENGTH: 35
<212> TYPE: DNA
<213> ORGANISM: Artificial Sequence
<220> FEATURE:
<223> OTHER INFORMATION: synthetic primer

<400> SEQUENCE: 43
gtggaaatca aacgaactgt ggctgcacca tctgt           35

<210> SEQ ID NO 44
<211> LENGTH: 25
<212> TYPE: DNA
<213> ORGANISM: Artificial Sequence
<220> FEATURE:
<223> OTHER INFORMATION: synthetic primer

<400> SEQUENCE: 44
aggtatttca ttttaaattc ctcct                      25

<210> SEQ ID NO 45
<211> LENGTH: 32
<212> TYPE: DNA
<213> ORGANISM: Artificial Sequence
<220> FEATURE:
<223> OTHER INFORMATION: synthetic primer

<400> SEQUENCE: 45

```
<210> SEQ ID NO 46
<211> LENGTH: 37
<212> TYPE: DNA
<213> ORGANISM: Artificial Sequence
<220> FEATURE:
<223> OTHER INFORMATION: synthetic primer

<400> SEQUENCE: 46
cttggtggag gctgaggaga cggtgaccgt ggtccct                              37

<210> SEQ ID NO 47
<211> LENGTH: 34
<212> TYPE: DNA
<213> ORGANISM: Artificial Sequence
<220> FEATURE:
<223> OTHER INFORMATION: synthetic primer

<400> SEQUENCE: 47
tggaggtgga tccgagctcg taatgacgca gtct                                 34

<210> SEQ ID NO 48
<211> LENGTH: 36
<212> TYPE: DNA
<213> ORGANISM: Artificial Sequence
<220> FEATURE:
<223> OTHER INFORMATION: synthetic primer

<400> SEQUENCE: 48
agccacagtt cgtttgattt ccaccttggt cccagg                               36
```

Also on this page at line 32:
```
gaggtgcagc tgctcgagac tggaggaggc tt                                   32
```